US008684994B2

(12) United States Patent
Lev et al.

(10) Patent No.: US 8,684,994 B2
(45) Date of Patent: Apr. 1, 2014

(54) FLUID TRANSFER ASSEMBLY WITH VENTING ARRANGEMENT

(75) Inventors: Nimrod Lev, Savion (IL); Niv Ben Shalom, Netanya (IL); Amir Lev, Kfar Saba (IL)

(73) Assignee: MEDIMOP Medical Projects Ltd., Ra'anana (IL)

( * ) Notice: Subject to any disclaimer, the term of this patent is extended or adjusted under 35 U.S.C. 154(b) by 0 days.

(21) Appl. No.: 13/522,410

(22) PCT Filed: Feb. 23, 2011

(86) PCT No.: PCT/IL2011/000186
§ 371 (c)(1), (2), (4) Date: Jul. 16, 2012

(87) PCT Pub. No.: WO2011/104711
PCT Pub. Date: Sep. 1, 2011

(65) Prior Publication Data

US 2012/0323210 A1 Dec. 20, 2012

(30) Foreign Application Priority Data

Feb. 24, 2010 (IL) ........................................ 204141

(51) Int. Cl.
*A61B 19/00* (2006.01)

(52) U.S. Cl.
USPC ............................ 604/415; 604/405; 604/416

(58) Field of Classification Search
None
See application file for complete search history.

(56) References Cited

U.S. PATENT DOCUMENTS

| | | | |
|---|---|---|---|
| 62,333 | A | 2/1867 | Holl |
| 1,021,681 | A | 3/1912 | Jennings |
| 1,704,817 | A | 3/1929 | Ayers |
| 1,930,944 | A | 10/1933 | Schmitz, Jr. |
| 2,326,490 | A | 8/1943 | Perelson |
| 2,931,668 | A | 4/1960 | Baley |
| 2,968,497 | A | 1/1961 | Treleman |
| 3,059,643 | A | 10/1962 | Barton |
| D198,499 | S | 6/1964 | Harautuneian |
| 3,484,849 | A | 12/1969 | Huebner et al. |
| 3,618,637 | A | 11/1971 | Santomieri |
| 3,757,981 | A | 9/1973 | Harris, Sr. et al. |
| 3,788,524 | A | 1/1974 | Davis et al. |
| 3,822,700 | A | 7/1974 | Pennington |

(Continued)

FOREIGN PATENT DOCUMENTS

| | | | |
|---|---|---|---|
| DE | 1913926 | A1 | 9/1970 |
| DE | 4122476 | A1 | 1/1993 |

(Continued)

OTHER PUBLICATIONS

Grifols Vial Adapter Product Literature, 2 pages, Jan. 2002.

(Continued)

*Primary Examiner* — Leslie Deak
(74) *Attorney, Agent, or Firm* — Panitch Schwarze Belisario & Nadel LLP

(57) ABSTRACT

A fluid transfer assembly including a vented female vial adapter and male vial adapter for use with a pair of vials including a vial with contents under negative pressure for liquid drug reconstitution and administration purposes. The vented female vial adapter includes a venting arrangement and the male vial adapter includes a sealing arrangement for selectively sealing the venting arrangement. The fluid transfer assembly is designed such that only filtered air is drawn into the vial under negative pressure subsequent to reconstitution of liquid drug contents to ensure sterile conditions.

10 Claims, 11 Drawing Sheets

(56) References Cited

U.S. PATENT DOCUMENTS

| | | | |
|---|---|---|---|
| 3,826,261 | A | 7/1974 | Killinger |
| 3,885,607 | A | 5/1975 | Peltier |
| 3,938,520 | A | 2/1976 | Scislowicz et al. |
| 3,957,052 | A | 5/1976 | Topham |
| 3,977,555 | A | 8/1976 | Larson |
| 3,993,063 | A | 11/1976 | Larrabee |
| 4,020,839 | A | 5/1977 | Klapp |
| 4,051,852 | A | 10/1977 | Villari |
| 4,109,670 | A | 8/1978 | Slagel |
| 4,121,585 | A | 10/1978 | Becker, Jr. |
| 4,161,178 | A | 7/1979 | Genese |
| 4,187,848 | A | 2/1980 | Taylor |
| 4,203,067 | A | 5/1980 | Fitzky et al. |
| 4,203,443 | A | 5/1980 | Genese |
| 4,210,173 | A | 7/1980 | Choksi et al. |
| D257,286 | S | 10/1980 | Folkman |
| 4,253,501 | A | 3/1981 | Ogle |
| 4,296,786 | A | 10/1981 | Brignola |
| 4,303,067 | A | 12/1981 | Connolly et al. |
| 4,312,349 | A | 1/1982 | Cohen |
| 4,314,586 | A | 2/1982 | Folkman |
| 4,328,802 | A | 5/1982 | Curley et al. |
| 4,335,717 | A | 6/1982 | Bujan et al. |
| D267,199 | S | 12/1982 | Koenig |
| 4,376,634 | A | 3/1983 | Prior et al. |
| D268,871 | S | 5/1983 | Benham et al. |
| 4,392,850 | A | 7/1983 | Elias et al. |
| 4,410,321 | A | 10/1983 | Pearson et al. |
| 4,411,662 | A | 10/1983 | Pearson |
| D271,421 | S | 11/1983 | Fetterman |
| 4,434,823 | A | 3/1984 | Hudspith |
| 4,465,471 | A | 8/1984 | Harris et al. |
| 4,475,915 | A | 10/1984 | Sloane |
| 4,493,348 | A | 1/1985 | Lemmons |
| 4,505,709 | A | 3/1985 | Froning et al. |
| 4,507,113 | A | 3/1985 | Dunlap |
| D280,018 | S | 8/1985 | Scott |
| 4,532,969 | A | 8/1985 | Kwaan |
| 4,564,054 | A | 1/1986 | Gustavsson |
| 4,573,993 | A | 3/1986 | Hoag et al. |
| 4,576,211 | A | 3/1986 | Valentini et al. |
| 4,581,014 | A | 4/1986 | Millerd et al. |
| 4,588,396 | A | 5/1986 | Stroebel et al. |
| 4,588,403 | A | 5/1986 | Weiss et al. |
| D284,603 | S | 7/1986 | Loignon |
| 4,604,093 | A | 8/1986 | Brown et al. |
| 4,607,671 | A | 8/1986 | Aalto et al. |
| 4,614,437 | A | 9/1986 | Buehler |
| 4,638,975 | A | 1/1987 | Iuchi et al. |
| 4,639,019 | A | 1/1987 | Mittleman |
| 4,667,927 | A | 5/1987 | Oscarsson |
| 4,676,530 | A | 6/1987 | Nordgren et al. |
| 4,683,975 | A | 8/1987 | Booth et al. |
| 4,697,622 | A | 10/1987 | Swift et al. |
| 4,721,133 | A | 1/1988 | Sundblom |
| 4,729,401 | A | 3/1988 | Raines |
| 4,735,608 | A | 4/1988 | Sardam |
| 4,743,229 | A | 5/1988 | Chu |
| 4,743,243 | A | 5/1988 | Vaillancourt |
| 4,752,292 | A | 6/1988 | Lopez et al. |
| 4,758,235 | A | 7/1988 | Tu |
| 4,759,756 | A | 7/1988 | Forman et al. |
| 4,778,447 | A | 10/1988 | Velde et al. |
| 4,787,898 | A | 11/1988 | Raines |
| 4,797,898 | A | 1/1989 | Martinez |
| 4,804,366 | A | 2/1989 | Zdeb et al. |
| 4,832,690 | A | 5/1989 | Kuu |
| 4,834,152 | A | 5/1989 | Howson et al. |
| 4,857,062 | A | 8/1989 | Russell |
| 4,865,592 | A | 9/1989 | Rycroft |
| 4,909,290 | A | 3/1990 | Coccia |
| 4,931,040 | A | 6/1990 | Haber et al. |
| 4,932,944 | A | 6/1990 | Jagger et al. |
| 4,967,797 | A | 11/1990 | Manska |
| D314,050 | S | 1/1991 | Sone |
| D314,622 | S | 2/1991 | Andersson et al. |
| 4,997,430 | A | 3/1991 | Van der Heiden et al. |
| 5,006,114 | A | 4/1991 | Rogers et al. |
| 5,035,686 | A | 7/1991 | Crittenden et al. |
| 5,041,105 | A | 8/1991 | D'Alo et al. |
| 5,045,066 | A | 9/1991 | Scheuble et al. |
| 5,049,129 | A | 9/1991 | Zdeb et al. |
| 5,053,015 | A | 10/1991 | Gross |
| 5,061,248 | A | 10/1991 | Sacco |
| 5,088,996 | A | 2/1992 | Kopfer et al. |
| 5,096,575 | A | 3/1992 | Cosack |
| 5,104,387 | A | 4/1992 | Pokorney et al. |
| 5,113,904 | A | 5/1992 | Aslanian |
| 5,122,124 | A | 6/1992 | Novacek et al. |
| 5,125,908 | A | 6/1992 | Cohen |
| 5,125,915 | A | 6/1992 | Berry et al. |
| D328,788 | S | 8/1992 | Sagae et al. |
| 5,171,230 | A | 12/1992 | Eland et al. |
| 5,201,705 | A | 4/1993 | Berglund et al. |
| 5,201,717 | A | 4/1993 | Wyatt et al. |
| 5,203,771 | A | 4/1993 | Melker et al. |
| 5,203,775 | A | 4/1993 | Frank et al. |
| 5,211,638 | A | 5/1993 | Dudar et al. |
| 5,232,029 | A | 8/1993 | Knox et al. |
| 5,232,109 | A | 8/1993 | Tirrell et al. |
| 5,242,432 | A | 9/1993 | DeFrank |
| 5,247,972 | A | 9/1993 | Tetreault |
| D341,420 | S | 11/1993 | Conn |
| 5,269,768 | A | 12/1993 | Cheung |
| 5,270,219 | A | 12/1993 | DeCastro et al. |
| 5,279,576 | A | 1/1994 | Loo et al. |
| 5,288,290 | A | 2/1994 | Brody |
| 5,300,034 | A | 4/1994 | Behnke et al. |
| 5,304,163 | A | 4/1994 | Bonnici et al. |
| 5,308,483 | A | 5/1994 | Sklar et al. |
| 5,312,377 | A | 5/1994 | Dalton |
| 5,328,474 | A | 7/1994 | Raines |
| D349,648 | S | 8/1994 | Tirrell et al. |
| 5,334,163 | A | 8/1994 | Sinnett |
| 5,334,179 | A | 8/1994 | Poli et al. |
| 5,342,346 | A | 8/1994 | Honda et al. |
| 5,344,417 | A | 9/1994 | Wadsworth, Jr. |
| 5,350,372 | A | 9/1994 | Ikeda et al. |
| 5,364,386 | A | 11/1994 | Fukuoka et al. |
| 5,364,387 | A | 11/1994 | Sweeney |
| 5,374,264 | A | 12/1994 | Wadsworth, Jr. |
| 5,385,547 | A | 1/1995 | Wong et al. |
| 5,397,303 | A | 3/1995 | Sancoff et al. |
| 5,429,614 | A | 7/1995 | Fowles et al. |
| 5,433,330 | A | 7/1995 | Yatsko et al. |
| 5,445,630 | A | 8/1995 | Richmond |
| 5,445,631 | A | 8/1995 | Uchida |
| 5,451,374 | A | 9/1995 | Molina |
| 5,454,805 | A | 10/1995 | Brony |
| 5,464,111 | A | 11/1995 | Vacek et al. |
| 5,464,123 | A | 11/1995 | Scarrow |
| 5,466,219 | A | 11/1995 | Lynn et al. |
| 5,466,220 | A | 11/1995 | Brenneman |
| 5,470,327 | A | 11/1995 | Helgren et al. |
| 5,478,337 | A | 12/1995 | Okamoto et al. |
| 5,492,147 | A | 2/1996 | Challender et al. |
| D369,406 | S | 4/1996 | Niedospial et al. |
| 5,505,714 | A | 4/1996 | Dassa et al. |
| 5,509,433 | A | 4/1996 | Paradis |
| 5,520,659 | A | 5/1996 | Hedges |
| 5,526,853 | A | 6/1996 | McPhee et al. |
| 5,527,306 | A | 6/1996 | Haining |
| 5,531,695 | A | 7/1996 | Swisher |
| 5,547,471 | A | 8/1996 | Thompson et al. |
| 5,549,577 | A | 8/1996 | Siegel et al. |
| 5,554,128 | A | 9/1996 | Hedges |
| 5,566,729 | A | 10/1996 | Grabenkort et al. |
| 5,569,191 | A | 10/1996 | Meyer |
| 5,573,281 | A | 11/1996 | Keller |
| 5,578,015 | A | 11/1996 | Robb |
| 5,583,052 | A | 12/1996 | Portnoff et al. |
| 5,584,819 | A | 12/1996 | Kopfer |
| 5,591,143 | A | 1/1997 | Trombley, III et al. |
| 5,603,706 | A | 2/1997 | Wyatt et al. |

(56) References Cited

U.S. PATENT DOCUMENTS

| | | | |
|---|---|---|---|
| 5,607,439 | A | 3/1997 | Yoon |
| 5,611,576 | A | 3/1997 | Guala |
| 5,616,203 | A | 4/1997 | Stevens |
| 5,636,660 | A | 6/1997 | Pfleiderer et al. |
| 5,641,010 | A | 6/1997 | Maier |
| 5,645,538 | A | 7/1997 | Richmond |
| 5,647,845 | A | 7/1997 | Haber et al. |
| 5,651,776 | A | 7/1997 | Appling et al. |
| 5,653,686 | A | 8/1997 | Coulter et al. |
| 5,674,195 | A | 10/1997 | Truthan |
| 5,676,346 | A | 10/1997 | Leinsing |
| 5,685,845 | A | 11/1997 | Grimard |
| 5,699,821 | A | 12/1997 | Paradis |
| 5,702,019 | A | 12/1997 | Grimard |
| 5,718,346 | A | 2/1998 | Weiler |
| D393,722 | S | 4/1998 | Fangrow, Jr. et al. |
| 5,738,144 | A | 4/1998 | Rogers |
| 5,743,312 | A | 4/1998 | Pfeifer et al. |
| 5,746,733 | A | 5/1998 | Capaccio et al. |
| 5,755,696 | A | 5/1998 | Caizza |
| 5,766,211 | A | 6/1998 | Wood et al. |
| 5,772,630 | A | 6/1998 | Ljungquist |
| 5,772,652 | A | 6/1998 | Zielinski |
| RE35,841 | E | 7/1998 | Frank et al. |
| 5,776,116 | A | 7/1998 | Lopez et al. |
| 5,782,872 | A | 7/1998 | Muller |
| 5,806,831 | A | 9/1998 | Paradis |
| 5,817,082 | A | 10/1998 | Niedospial, Jr. et al. |
| 5,820,621 | A | 10/1998 | Yale et al. |
| 5,827,262 | A | 10/1998 | Neftel et al. |
| 5,832,971 | A | 11/1998 | Yale et al. |
| 5,833,213 | A | 11/1998 | Ryan |
| 5,834,744 | A | 11/1998 | Risman |
| 5,839,715 | A | 11/1998 | Leinsing |
| 5,853,406 | A | 12/1998 | Masuda et al. |
| 5,871,110 | A | 2/1999 | Grimard et al. |
| 5,873,872 | A | 2/1999 | Thibault et al. |
| 5,879,337 | A | 3/1999 | Kuracina et al. |
| 5,879,345 | A | 3/1999 | Aneas |
| 5,887,633 | A | 3/1999 | Yale et al. |
| 5,890,610 | A | 4/1999 | Jansen et al. |
| 5,891,129 | A | 4/1999 | Daubert et al. |
| 5,893,397 | A | 4/1999 | Peterson et al. |
| 5,897,526 | A | 4/1999 | Vaillancourt |
| 5,899,468 | A | 5/1999 | Apps et al. |
| 5,902,280 | A | 5/1999 | Powles et al. |
| 5,902,298 | A | 5/1999 | Niedospial, Jr. et al. |
| 5,911,710 | A | 6/1999 | Barry et al. |
| 5,919,182 | A | 7/1999 | Avallone |
| 5,921,419 | A | 7/1999 | Niedospial, Jr. et al. |
| 5,924,584 | A | 7/1999 | Hellstrom et al. |
| 5,925,029 | A | 7/1999 | Jansen et al. |
| 5,935,112 | A | 8/1999 | Stevens et al. |
| 5,941,848 | A | 8/1999 | Nishimoto et al. |
| 5,944,700 | A | 8/1999 | Nguyen et al. |
| 5,954,104 | A | 9/1999 | Daubert et al. |
| 5,971,181 | A | 10/1999 | Niedospial, Jr. et al. |
| 5,971,965 | A | 10/1999 | Mayer |
| 5,989,237 | A | 11/1999 | Fowles et al. |
| 6,003,566 | A | 12/1999 | Thibault et al. |
| 6,004,278 | A | 12/1999 | Botich et al. |
| 6,019,750 | A | 2/2000 | Fowles et al. |
| 6,022,339 | A | 2/2000 | Fowles et al. |
| 6,036,171 | A | 3/2000 | Weinheimer et al. |
| 6,039,093 | A | 3/2000 | Mrotzek et al. |
| 6,039,302 | A | 3/2000 | Cote, Sr. et al. |
| D422,357 | S | 4/2000 | Niedospial, Jr. et al. |
| 6,063,068 | A | 5/2000 | Fowles et al. |
| D427,308 | S | 6/2000 | Zinger |
| 6,070,623 | A | 6/2000 | Aneas |
| 6,071,270 | A | 6/2000 | Fowles et al. |
| 6,080,132 | A | 6/2000 | Cole et al. |
| 6,089,541 | A | 7/2000 | Weinheimer et al. |
| 6,090,091 | A | 7/2000 | Fowles et al. |
| 6,090,093 | A | 7/2000 | Thibault et al. |
| 6,099,511 | A | 8/2000 | Devos et al. |
| 6,113,068 | A | 9/2000 | Ryan |
| 6,113,583 | A | 9/2000 | Fowles et al. |
| 6,117,114 | A | 9/2000 | Paradis |
| 6,139,534 | A | 10/2000 | Niedospial, Jr. et al. |
| 6,142,446 | A | 11/2000 | Leinsing |
| 6,146,362 | A | 11/2000 | Turnbull et al. |
| 6,156,025 | A | 12/2000 | Niedospial, Jr. et al. |
| 6,159,192 | A | 12/2000 | Fowles et al. |
| 6,168,037 | B1 | 1/2001 | Grimard |
| 6,171,287 | B1 | 1/2001 | Lynn et al. |
| 6,171,293 | B1 | 1/2001 | Rowley et al. |
| 6,173,852 | B1 | 1/2001 | Browne |
| 6,174,304 | B1 | 1/2001 | Weston |
| 6,179,822 | B1 | 1/2001 | Niedospial, Jr. |
| 6,179,823 | B1 | 1/2001 | Niedospial, Jr. |
| 6,206,861 | B1 | 3/2001 | Mayer |
| 6,221,041 | B1 | 4/2001 | Russo |
| 6,221,054 | B1 | 4/2001 | Martin et al. |
| 6,221,065 | B1 | 4/2001 | Davis |
| 6,238,372 | B1 | 5/2001 | Zinger et al. |
| 6,245,044 | B1 | 6/2001 | Daw et al. |
| D445,501 | S | 7/2001 | Niedospial, Jr. |
| D445,895 | S | 7/2001 | Svendsen |
| 6,253,804 | B1 | 7/2001 | Safabash |
| 6,258,078 | B1 | 7/2001 | Thilly |
| 6,280,430 | B1 | 8/2001 | Neftel et al. |
| 6,290,688 | B1 | 9/2001 | Lopez et al. |
| 6,296,621 | B1 | 10/2001 | Masuda et al. |
| 6,299,131 | B1 | 10/2001 | Ryan |
| 6,343,629 | B1 | 2/2002 | Wessman et al. |
| 6,348,044 | B1 | 2/2002 | Coletti et al. |
| 6,358,236 | B1 | 3/2002 | DeFoggi et al. |
| 6,364,866 | B1 | 4/2002 | Furr et al. |
| 6,378,576 | B2 | 4/2002 | Thibault et al. |
| 6,378,714 | B1 | 4/2002 | Jansen et al. |
| 6,379,340 | B1 | 4/2002 | Zinger et al. |
| 6,382,442 | B1 | 5/2002 | Thibault et al. |
| 6,408,897 | B1 | 6/2002 | Laurent et al. |
| 6,409,708 | B1 | 6/2002 | Wessman |
| 6,440,107 | B1 | 8/2002 | Trombley, III et al. |
| 6,453,949 | B1 | 9/2002 | Chau |
| 6,453,956 | B2 | 9/2002 | Safabash |
| 6,474,375 | B2 | 11/2002 | Spero et al. |
| 6,478,788 | B1 | 11/2002 | Aneas |
| D468,015 | S | 12/2002 | Horppu |
| 6,499,617 | B1 | 12/2002 | Niedospial, Jr. et al. |
| 6,503,240 | B1 | 1/2003 | Niedospial, Jr. et al. |
| 6,503,244 | B2 | 1/2003 | Hayman |
| 6,520,932 | B2 | 2/2003 | Taylor |
| 6,524,278 | B1 | 2/2003 | Campbell et al. |
| 6,524,295 | B2 | 2/2003 | Daubert et al. |
| D472,316 | S | 3/2003 | Douglas et al. |
| 6,530,903 | B2 | 3/2003 | Wang et al. |
| 6,537,263 | B1 | 3/2003 | Aneas |
| D472,630 | S | 4/2003 | Douglas et al. |
| 6,544,246 | B1 | 4/2003 | Niedospial, Jr. |
| 6,551,299 | B2 | 4/2003 | Miyoshi et al. |
| 6,558,365 | B2 | 5/2003 | Zinger et al. |
| 6,571,837 | B2 | 6/2003 | Jansen et al. |
| 6,572,591 | B2 | 6/2003 | Mayer |
| 6,575,955 | B2 | 6/2003 | Azzolini |
| 6,581,593 | B1 | 6/2003 | Rubin et al. |
| 6,582,415 | B1 | 6/2003 | Fowles et al. |
| 6,591,876 | B2 | 7/2003 | Safabash |
| 6,601,721 | B2 | 8/2003 | Jansen et al. |
| 6,626,309 | B1 | 9/2003 | Jansen et al. |
| D482,121 | S | 11/2003 | Harding et al. |
| D482,447 | S | 11/2003 | Harding et al. |
| 6,651,956 | B2 | 11/2003 | Miller |
| 6,652,509 | B1 | 11/2003 | Helgren et al. |
| D483,487 | S | 12/2003 | Harding et al. |
| D483,869 | S | 12/2003 | Tran et al. |
| 6,656,433 | B2 | 12/2003 | Sasso |
| 6,666,852 | B2 | 12/2003 | Niedospial, Jr. |
| 6,681,810 | B2 | 1/2004 | Weston |
| 6,681,946 | B1 | 1/2004 | Jansen et al. |
| 6,682,509 | B2 | 1/2004 | Lopez |
| 6,692,478 | B1 | 2/2004 | Paradis |

(56) References Cited

U.S. PATENT DOCUMENTS 6,692,829 B2 2/2004 Stubler et al.
6,695,829 B2 2/2004 Hellstrom et al.
6,699,229 B2 3/2004 Zinger et al.
6,706,022 B1 3/2004 Leinsing et al.
6,706,031 B2 3/2004 Manera
6,715,520 B2 4/2004 Andreasson et al.
6,729,370 B2 5/2004 Norton et al.
6,736,798 B2 5/2004 Ohkubo et al.
6,745,998 B2 6/2004 Doyle
6,746,438 B1 6/2004 Arnissolle
6,752,180 B2 6/2004 Delay
D495,416 S 8/2004 Dimeo et al.
D496,457 S 9/2004 Prais et al.
6,802,490 B2 10/2004 Leinsing et al.
6,832,994 B2 12/2004 Niedospial, Jr. et al.
6,852,103 B2 2/2005 Fowles et al.
6,875,203 B1 4/2005 Fowles et al.
6,875,205 B2 4/2005 Leinsing
6,878,131 B2 4/2005 Novacek et al.
6,890,328 B2 5/2005 Fowles et al.
6,901,975 B2 6/2005 Aramata et al.
6,945,417 B2 9/2005 Jansen et al.
6,948,522 B2 9/2005 Newbrough et al.
6,949,086 B2 9/2005 Ferguson et al.
6,957,745 B2 10/2005 Thibault et al.
RE38,996 E 2/2006 Crawford et al.
6,994,315 B2 2/2006 Ryan et al.
6,997,916 B2 2/2006 Simas, Jr. et al.
6,997,917 B2 2/2006 Niedospial, Jr. et al.
7,024,968 B2 4/2006 Raudabough et al.
7,070,589 B2 7/2006 Lolachi et al.
7,074,216 B2 7/2006 Fowles et al.
7,083,600 B2 8/2006 Meloul
7,086,431 B2 8/2006 D'Antonio et al.
7,100,890 B2 9/2006 Cote, Sr. et al.
7,150,735 B2 12/2006 Hickle
7,192,423 B2 3/2007 Wong
7,195,623 B2 3/2007 Burroughs et al.
7,241,285 B1 7/2007 Dikeman
7,294,122 B2 11/2007 Kubo et al.
7,306,199 B2 12/2007 Leinsing et al.
D561,348 S 2/2008 Zinger et al.
7,326,188 B1 2/2008 Russell et al.
7,326,194 B2 2/2008 Zinger et al.
7,350,764 B2 4/2008 Raybuck
7,354,422 B2 4/2008 Riesenberger et al.
7,354,427 B2 4/2008 Fangrow
7,425,209 B2 9/2008 Fowles et al.
7,435,246 B2 10/2008 Zihlmann
7,452,348 B2 11/2008 Hasegawa
7,470,257 B2 12/2008 Norton et al.
7,470,265 B2 12/2008 Brugger et al.
7,472,932 B2 1/2009 Weber et al.
7,488,297 B2 2/2009 Flaherty
7,491,197 B2 2/2009 Jansen et al.
7,497,848 B2 3/2009 Leinsing et al.
7,523,967 B2 4/2009 Steppe
7,530,546 B2 5/2009 Ryan et al.
D595,420 S 6/2009 Suzuki et al.
D595,421 S 6/2009 Suzuki et al.
7,540,863 B2 6/2009 Haindl
7,540,865 B2 6/2009 Griffin et al.
7,544,191 B2 6/2009 Peluso et al.
D595,862 S 7/2009 Suzuki et al.
D595,863 S 7/2009 Suzuki et al.
7,611,487 B2 11/2009 Woehr et al.
7,611,502 B2 11/2009 Daly
7,615,041 B2 11/2009 Sullivan et al.
7,628,779 B2 12/2009 Aneas
7,632,261 B2 12/2009 Zinger et al.
D608,900 S 1/2010 Giraud et al.
7,654,995 B2 2/2010 Warren et al.
7,695,445 B2 4/2010 Yuki
D616,090 S 5/2010 Kawamura
7,713,247 B2 5/2010 Lopez
7,717,886 B2 5/2010 Lopez
7,722,090 B2 5/2010 Burton et al.
D616,984 S 6/2010 Gilboa
7,731,678 B2 6/2010 Tennican et al.
7,743,799 B2 6/2010 Mosler et al.
7,758,082 B2 7/2010 Weigel et al.
7,762,524 B2 7/2010 Cawthon et al.
7,766,304 B2 8/2010 Phillips
7,771,383 B2 8/2010 Truitt et al.
7,799,009 B2 9/2010 Niedospial, Jr. et al.
7,803,140 B2 9/2010 Fangrow, Jr.
D627,216 S 11/2010 Fulginiti
D630,732 S 1/2011 Lev et al.
7,862,537 B2 1/2011 Zinger et al.
7,867,215 B2 1/2011 Akerlund et al.
7,879,018 B2 2/2011 Zinger et al.
D634,007 S 3/2011 Zinger et al.
7,900,659 B2 3/2011 Whitley et al.
D637,713 S 5/2011 Nord et al.
D644,104 S 8/2011 Maeda et al.
7,993,328 B2 8/2011 Whitley
8,016,809 B2 9/2011 Zinger et al.
8,025,653 B2 9/2011 Capitaine et al.
8,029,472 B2 10/2011 Leinsing et al.
8,038,123 B2 10/2011 Ruschke et al.
8,066,688 B2 11/2011 Zinger et al.
8,070,739 B2 12/2011 Zinger et al.
8,096,525 B2 1/2012 Ryan
8,105,314 B2 1/2012 Fangrow, Jr.
D655,017 S 2/2012 Mosler et al.
8,122,923 B2 2/2012 Kraus et al.
D655,071 S 3/2012 Davila
8,157,784 B2 4/2012 Rogers
8,167,863 B2 5/2012 Yow
8,172,824 B2 5/2012 Pfeifer et al.
8,177,768 B2 5/2012 Leinsing
8,182,452 B2 5/2012 Mansour et al.
8,197,459 B2 6/2012 Jansen et al.
8,211,069 B2 7/2012 Fangrow, Jr.
8,225,959 B2 7/2012 Lambrecht
8,241,268 B2 8/2012 Whitley
8,262,628 B2 9/2012 Fangrow, Jr.
D669,980 S 10/2012 Lev et al.
8,287,513 B2 10/2012 Ellstrom et al.
D674,088 S 1/2013 Lev et al.
8,480,646 B2 7/2013 Nord et al.
8,506,548 B2 8/2013 Okiyama
8,523,837 B2 9/2013 Wiggins et al.
8,545,476 B2 10/2013 Ariagno et al.
8,551,067 B2 10/2013 Zinger et al.
8,556,879 B2 10/2013 Okiyama
2001/0000347 A1 4/2001 Hellstrom et al.
2001/0025671 A1 10/2001 Safabash
2001/0029360 A1 10/2001 Miyoshi et al.
2001/0051793 A1 12/2001 Weston
2002/0017328 A1 2/2002 Loo
2002/0066715 A1 6/2002 Niedospial
2002/0087118 A1 7/2002 Reynolds et al.
2002/0087141 A1 7/2002 Zinger et al.
2002/0087144 A1 7/2002 Zinger et al.
2002/0121496 A1 9/2002 Thiebault et al.
2002/0123736 A1 9/2002 Fowles et al.
2002/0127150 A1 9/2002 Sasso
2002/0128628 A1 9/2002 Fathallah
2002/0173752 A1 11/2002 Polzin
2002/0193777 A1 12/2002 Aneas
2003/0028156 A1 2/2003 Juliar
2003/0036725 A1 2/2003 Lavi et al.
2003/0068354 A1 4/2003 Reif et al.
2003/0073971 A1 4/2003 Saker
2003/0100866 A1 5/2003 Reynolds
2003/0120209 A1 6/2003 Jensen et al.
2003/0153895 A1 8/2003 Leinsing
2003/0187420 A1 10/2003 Akerlund et al.
2003/0191445 A1 10/2003 Wallen et al.
2003/0195479 A1 10/2003 Kuracina et al.
2003/0199846 A1 10/2003 Fowles et al.
2003/0199847 A1 10/2003 Akerlund et al.
2004/0024354 A1 2/2004 Reynolds

(56) References Cited

U.S. PATENT DOCUMENTS

| | | | |
|---|---|---|---|
| 2004/0044327 | A1 | 3/2004 | Hasegawa |
| 2004/0073189 | A1 | 4/2004 | Wyatt et al. |
| 2004/0153047 | A1 | 8/2004 | Blank et al. |
| 2004/0181192 | A1 | 9/2004 | Cuppy |
| 2004/0204699 | A1 | 10/2004 | Hanly et al. |
| 2004/0217315 | A1 | 11/2004 | Doyle |
| 2004/0236305 | A1 | 11/2004 | Jansen et al. |
| 2005/0015070 | A1 | 1/2005 | Delnevo et al. |
| 2005/0055008 | A1 | 3/2005 | Paradis et al. |
| 2005/0124964 | A1 | 6/2005 | Niedospial et al. |
| 2005/0137566 | A1 | 6/2005 | Fowles et al. |
| 2005/0148994 | A1 | 7/2005 | Leinsing |
| 2005/0159724 | A1 | 7/2005 | Enerson |
| 2005/0182383 | A1 | 8/2005 | Wallen |
| 2005/0261637 | A1 | 11/2005 | Miller |
| 2006/0030832 | A1 | 2/2006 | Niedospial et al. |
| 2006/0079834 | A1 | 4/2006 | Tennican et al. |
| 2006/0089594 | A1 | 4/2006 | Landau |
| 2006/0089603 | A1 | 4/2006 | Truitt et al. |
| 2006/0095015 | A1 | 5/2006 | Hobbs et al. |
| 2006/0106360 | A1 | 5/2006 | Wong |
| 2006/0135948 | A1 | 6/2006 | Varma |
| 2006/0253084 | A1 | 11/2006 | Nordgren |
| 2007/0024995 | A1 | 2/2007 | Hayashi |
| 2007/0060904 | A1 | 3/2007 | Vedrine et al. |
| 2007/0079894 | A1 | 4/2007 | Kraus et al. |
| 2007/0083164 | A1 | 4/2007 | Barrelle et al. |
| 2007/0088252 | A1 | 4/2007 | Pestotnik et al. |
| 2007/0088293 | A1 | 4/2007 | Fangrow |
| 2007/0088313 | A1 | 4/2007 | Zinger et al. |
| 2007/0106244 | A1 | 5/2007 | Mosler et al. |
| 2007/0112324 | A1 | 5/2007 | Hamedi-Sangsari |
| 2007/0156112 | A1 | 7/2007 | Walsh |
| 2007/0167904 | A1 | 7/2007 | Zinger et al. |
| 2007/0191760 | A1 | 8/2007 | Iguchi et al. |
| 2007/0191764 | A1 | 8/2007 | Zihlmann |
| 2007/0191767 | A1 | 8/2007 | Hennessy et al. |
| 2007/0219483 | A1 | 9/2007 | Kitani et al. |
| 2007/0244461 | A1 | 10/2007 | Fangrow |
| 2007/0244462 | A1 | 10/2007 | Fangrow |
| 2007/0244463 | A1 | 10/2007 | Warren et al. |
| 2007/0249995 | A1 | 10/2007 | Van Manen |
| 2007/0255202 | A1 | 11/2007 | Kitani et al. |
| 2007/0265574 | A1 | 11/2007 | Tennican et al. |
| 2007/0265581 | A1 | 11/2007 | Funamura et al. |
| 2007/0270778 | A9 | 11/2007 | Zinger et al. |
| 2007/0287953 | A1 | 12/2007 | Ziv et al. |
| 2007/0299404 | A1 | 12/2007 | Katoh et al. |
| 2008/0009789 | A1 | 1/2008 | Zinger et al. |
| 2008/0009822 | A1 | 1/2008 | Enerson |
| 2008/0172024 | A1 | 7/2008 | Yow |
| 2008/0249479 | A1 | 10/2008 | Zinger et al. |
| 2008/0249498 | A1 | 10/2008 | Fangrow |
| 2008/0287905 | A1 | 11/2008 | Hiejima et al. |
| 2008/0294100 | A1 | 11/2008 | de Costa et al. |
| 2008/0306439 | A1 | 12/2008 | Nelson et al. |
| 2008/0312634 | A1 | 12/2008 | Helmerson et al. |
| 2009/0012492 | A1 | 1/2009 | Zihlmann |
| 2009/0082750 | A1 | 3/2009 | Denenburg et al. |
| 2009/0143758 | A1 | 6/2009 | Okiyama |
| 2009/0177177 | A1 | 7/2009 | Zinger et al. |
| 2009/0177178 | A1 | 7/2009 | Pedersen |
| 2009/0187140 | A1 | 7/2009 | Racz |
| 2009/0216212 | A1 | 8/2009 | Fangrow, Jr. |
| 2009/0267011 | A1 | 10/2009 | Hatton et al. |
| 2009/0299325 | A1 | 12/2009 | Vedrine et al. |
| 2009/0326506 | A1 | 12/2009 | Hasegawa et al. |
| 2010/0010443 | A1 | 1/2010 | Morgan et al. |
| 2010/0022985 | A1 | 1/2010 | Sullivan et al. |
| 2010/0030181 | A1 | 2/2010 | Helle et al. |
| 2010/0036319 | A1 | 2/2010 | Drake et al. |
| 2010/0076397 | A1 | 3/2010 | Reed et al. |
| 2010/0087786 | A1 | 4/2010 | Zinger et al. |
| 2010/0137827 | A1 | 6/2010 | Warren et al. |
| 2010/0168712 | A1 | 7/2010 | Tuckwell et al. |
| 2010/0179506 | A1 | 7/2010 | Shemesh et al. |
| 2010/0204670 | A1 | 8/2010 | Kraushaar et al. |
| 2010/0241088 | A1 | 9/2010 | Ranalletta et al. |
| 2010/0274184 | A1 | 10/2010 | Chun |
| 2010/0286661 | A1 | 11/2010 | Raday et al. |
| 2010/0312220 | A1 | 12/2010 | Kalitzki |
| 2011/0054440 | A1 | 3/2011 | Lewis |
| 2011/0224640 | A1 | 9/2011 | Kuhn et al. |
| 2011/0230856 | A1 | 9/2011 | Kyle et al. |
| 2011/0264069 | A1 | 10/2011 | Bochenko |
| 2011/0276007 | A1 | 11/2011 | Denenburg |
| 2011/0319827 | A1 | 12/2011 | Leinsing et al. |
| 2012/0022469 | A1 | 1/2012 | Alpert |
| 2012/0053555 | A1 | 3/2012 | Ariagno et al. |
| 2012/0059346 | A1 | 3/2012 | Sheppard et al. |
| 2012/0078214 | A1 | 3/2012 | Finke et al. |
| 2012/0123382 | A1 | 5/2012 | Kubo |
| 2012/0184938 | A1 | 7/2012 | Lev et al. |
| 2012/0215182 | A1 | 8/2012 | Mansour et al. |
| 2012/0220977 | A1 | 8/2012 | Yow |
| 2012/0220978 | A1 | 8/2012 | Lev et al. |
| 2012/0265163 | A1 | 10/2012 | Cheng et al. |
| 2012/0310203 | A1 | 12/2012 | Khaled et al. |
| 2013/0053814 | A1 | 2/2013 | Mueller-Beckhaus et al. |
| 2013/0096493 | A1 | 4/2013 | Kubo et al. |
| 2013/0199669 | A1 | 8/2013 | Moy et al. |

FOREIGN PATENT DOCUMENTS

| | | | |
|---|---|---|---|
| DE | 19504413 | A1 | 8/1996 |
| DE | 202004012714 | U1 | 11/2004 |
| DE | 202009011019 | U1 | 12/2010 |
| EP | 0192661 | A1 | 9/1986 |
| EP | 0195018 | A1 | 9/1986 |
| EP | 0258913 | A2 | 3/1988 |
| EP | 0416454 | A2 | 3/1991 |
| EP | 0518397 | A1 | 12/1992 |
| EP | 0521460 | A1 | 1/1993 |
| EP | 0637443 | A1 | 2/1995 |
| EP | 0737467 | A1 | 10/1996 |
| EP | 761562 | A1 | 3/1997 |
| EP | 765652 | A1 | 4/1997 |
| EP | 765853 | A1 | 4/1997 |
| EP | 0806597 | A1 | 11/1997 |
| EP | 0814866 | A1 | 1/1998 |
| EP | 829248 | A2 | 3/1998 |
| EP | 0856331 | A2 | 8/1998 |
| EP | 882441 | A2 | 12/1998 |
| EP | 897708 | A2 | 2/1999 |
| EP | 0898951 | A2 | 3/1999 |
| EP | 960616 | A2 | 12/1999 |
| EP | 1008337 | A1 | 6/2000 |
| EP | 1029526 | A1 | 8/2000 |
| EP | 1034809 | A1 | 9/2000 |
| EP | 1051988 | A2 | 11/2000 |
| EP | 1323403 | A1 | 7/2003 |
| EP | 1329210 | A1 | 7/2003 |
| EP | 1396250 | A1 | 3/2004 |
| EP | 1454609 | A1 | 9/2004 |
| EP | 1454650 | A1 | 9/2004 |
| EP | 1498097 | A2 | 1/2005 |
| EP | 1872824 | A1 | 1/2008 |
| EP | 1919432 | A1 | 5/2008 |
| EP | 1930038 | A2 | 6/2008 |
| EP | 2351548 | A1 | 8/2011 |
| EP | 2351549 | A1 | 8/2011 |
| FR | 2029242 | A5 | 10/1970 |
| FR | 2856660 | A1 | 12/2004 |
| FR | 2869795 | A1 | 11/2005 |
| FR | 2931363 | A1 | 11/2009 |
| GB | 1444210 | A | 7/1976 |
| IL | 171662 | | 10/2005 |
| JP | 03-062426 | B | 9/1991 |
| JP | 4329954 | A | 11/1992 |
| JP | 06-050656 | U | 7/1994 |
| JP | H08-000710 | A | 1/1996 |
| JP | 09-104460 | A | 4/1997 |
| JP | 09-104461 | A | 4/1997 |
| JP | 10-118158 | A | 5/1998 |

(56) References Cited

FOREIGN PATENT DOCUMENTS

| | | | |
|---|---|---|---|
| JP | H10-504736 | A | 5/1998 |
| JP | 11503627 | T | 3/1999 |
| JP | 11-319031 | A | 11/1999 |
| JP | 2000-508934 | A | 7/2000 |
| JP | 2000-237278 | A | 9/2000 |
| JP | 2001-505083 | A | 4/2001 |
| JP | 2002-035140 | A | 2/2002 |
| JP | 2002-516160 | A | 6/2002 |
| JP | 2002-355318 | A | 12/2002 |
| JP | 2003-033441 | A | 2/2003 |
| JP | 2003-102807 | A | 4/2003 |
| JP | 2004-097253 | A | 4/2004 |
| JP | 2004-522541 | A | 7/2004 |
| WO | 9403373 | A1 | 2/1994 |
| WO | 9507066 | A1 | 3/1995 |
| WO | 9600053 | A1 | 1/1996 |
| WO | 96/29113 | A1 | 9/1996 |
| WO | 9736636 | A1 | 10/1997 |
| WO | 9832411 | A1 | 7/1998 |
| WO | 9837854 | A1 | 9/1998 |
| WO | 9961093 | A1 | 12/1999 |
| WO | 0128490 | A1 | 4/2001 |
| WO | 0130425 | A1 | 5/2001 |
| WO | 0132524 | A1 | 5/2001 |
| WO | 0160311 | A1 | 8/2001 |
| WO | 0191693 | A2 | 12/2001 |
| WO | 0209797 | A1 | 2/2002 |
| WO | 0236191 | A2 | 5/2002 |
| WO | 02089900 | A1 | 11/2002 |
| WO | 03051423 | A2 | 6/2003 |
| WO | 03079956 | A1 | 10/2003 |
| WO | 2004041148 | A1 | 5/2004 |
| WO | 2005002492 | A1 | 1/2005 |
| WO | 2005041846 | A2 | 5/2005 |
| WO | 2005105014 | A2 | 11/2005 |
| WO | 2006099441 | A2 | 9/2006 |
| WO | 2007015233 | A1 | 2/2007 |
| WO | 2007017868 | A1 | 2/2007 |
| WO | 2007052252 | A1 | 5/2007 |
| WO | 2007105221 | A1 | 9/2007 |
| WO | 2009026443 | A2 | 2/2009 |
| WO | 2009029010 | A1 | 3/2009 |
| WO | 2009038860 | A1 | 3/2009 |
| WO | 2009038860 | A2 | 3/2009 |
| WO | 2009040804 | A2 | 4/2009 |
| WO | 2009087572 | A1 | 7/2009 |
| WO | 2009093249 | A1 | 7/2009 |
| WO | 2009112489 | A1 | 9/2009 |
| WO | 2009146088 | A1 | 12/2009 |
| WO | 2011058545 | A1 | 5/2011 |
| WO | 2011058548 | A1 | 5/2011 |
| WO | 2011077434 | A1 | 6/2011 |
| WO | 2011104711 | A1 | 9/2011 |
| WO | 2012143921 | A1 | 10/2012 |

OTHER PUBLICATIONS

Novel Transfer, Mixing and Drug Delivery Systems, MOP Medimop Medical Projects Ltd. Catalog, 4 pages, Rev. 4, 2004.
Smart Site.RTM. Alaris Medical Systems Product Brochure, 4 pages, Issue 1, Oct. 1999.
Smart Site.RTM. Needle-Free Systems, Alaris Medical Systems Webpage, 4 pages, Feb. 2006.
Photographs of Alaris Medical Systems SmartSite.RTM. device, 5 pages, 2002.
Non-Vented Vial Access Pin with ULTRASITE.RTM. Valve, B. Braun Medical, Inc. website and product description, 3 pages, Feb. 2006.
Office Action Issued Oct. 6, 2003 in U.S. Appl. No. 10/062,796.
Office Action Issued Feb. 22, 2005 in U.S. Appl. No. 10/062,796.
Office Action Issued Oct. 5, 2005 in U.S. Appl. No. 10/062,796.
Office Action Issued Feb. 20, 2009 in U.S. Appl. No. 11/694,297.
Int'l Search Report Issued Dec. 6, 2006 in Int'l Application No. PCT/IL2006/000912.
Int'l Preliminary Report on Patentability Issued Dec. 4, 2007 in Int'l Application No. PCT/IL2006/000912.
Int'l Search Report Issued Jul. 27, 2007 in Int'l Application No. PCT/IL2007/000343.
Int'l Preliminary Report on Patentability Issued Jun. 19, 2008 in Int'l Application No. PCT/IL2007/000343.
Int'l Search Report Issued Mar. 27, 2009 in Int'l Application No. PCT/US2008/070024.
Int'l Search Report Issued Oct. 17, 2005 in Int'l Application No. PCT/IL2005/000376.
Int'l Preliminary Report on Patentability Issued Jun. 19, 2006 in Int'l Application No. PCT/IL2005/000376.
Int'l Search Report Issued Aug. 25, 2008 in Int'l Application No. PCT/IL2008/000517.
Written Opinion of the ISR Issued Oct. 17, 2009 in Int'l Application No. PCT/IL08/00517.
Int'l Preliminary Report on Patenability Issued Oct. 20, 2009 in Int'l Application No. PCT/IL2008/000517.
Written Opinion of the Int'l Searching Authority Issued Oct. 27, 2008 in Int'l Application No. PCT/US2008/070024.
Int'l Search Report Issued Mar. 12, 2009 in Int'l Application No. PCT/IL2008/001278.
Office Action Issued Jan. 20, 2010 in JP Application No. 2007-510229.
Office Action Issued Apr. 20, 2010 in U.S. Appl. No. 11/997,569.
Int'l Search Report dated Nov. 20, 2006 in Int'l Application No. PCT/IL2006/000881.
Office Action Issued May 27, 2010 in U.S. Appl. No. 11/559,152.
Decision to Grant mailed Apr. 12, 2010 in EP Application No. 08738307.1.
Office Action issued Jun. 1, 2010 in U.S. Appl. No. 11/568,421.
Office Action issued Nov. 12, 2010 in U.S. Appl. No. 29/334,697.
The MixJect transfer system, as shown in the article, "Advanced Delivery Devices," Drug Delivery Technology Jul./Aug. 2007 vol. 7 No. 7 [on-line]. [Retrieved from Internet May 14, 2010.] URL: <http://www.drugdeiverytech-online.com/drugdelivery/200707/?pg=28pg28>. (3 pages).
Publication date of Israeli Patent Application 186290 [on-line]. [Retrieved from Internet May 24, 2010]. URL:<http://www.ilpatsearch.justrice.gov.il/UI/RequestsList.aspx>. (1 page).
Int'l Search Report issued Nov. 25, 2010 in Int'l Application No. PCT/IL2010/000530.
Office Action issued Feb. 7, 2011 in U.S. Appl. No. 12/783,194.
Office Action issued Dec. 20, 2010 in U.S. Appl. No. 12/063,176.
Office Action issued Dec. 13, 2010 in U.S. Appl. No. 12/293,122.
Office Action issued Nov. 29, 2010 in U.S. Appl. No. 11/568,421.
Office Action issued Dec. 23, 2010 in U.S. Appl. No. 29/334,696.
Int'l Search Report issued on Mar. 17, 2011 in Int'l Application No. PCT/IL2010/000854.
http://www.knovel.com/web/portal/browse/display?_EXT_KNOVEL_DISPLAY_bookid=1023&VerticalID=0 [retrieved on Feb. 9, 2011].
Int'l Search Report issued on Mar. 17, 2011 in Int'l Application No. PCT/IL2010/00915.
Office Action Issued May 12, 2011 in U.S. Appl. No. 12/063,176.
Office Action issued Jul. 11, 2011 in U.S. Appl. No. 12/293,122.
Int'l Search Report issued Jul. 12, 2011 in Int'l Application No. PCT/IL2011/000187.
Int'l Search Report issued Jul. 12, 2011 in Int'l Application No. PCT/IL2011/000186.
Office Action issued Aug. 3, 2011 in JP Application No. 2008-525719.
Int'l Search Report issued Oct. 7, 2011 in Int'l Application No. PCT/IL2011/000511.
Int'l Search Report issued Mar. 6, 2012 in Int'l Application No. PCT/IL2011/000834; Written Opinion.
Int'l Search Report issued Jan. 22, 2013 in Int'l Application No. PCT/IL2012/000354.
Int'l Search Report issued Mar. 18, 2013 in Int'l Application No. PCT/IL2012/050516.
Office Action issued Apr. 2, 2013 in U.S. Appl. No. 13/505,790.
Int'l Search Report and Written Opinion issued Mar. 6, 2012 in Int'l Application No. PCT/IL2011/000834.

(56) References Cited

OTHER PUBLICATIONS

U.S. Appl. No. 13/883,289 by Lev, filed May 3, 2013.
Int'l Search Report issued Jun. 5, 2013 in Int'l Application No. PCT/IL2012/050407.
Int'l Search Report issued Jun. 19, 2013 in Int'l Application No. PCT/IL201/050167.
Int'l Search Report issued Jul. 1, 2013 in Int'l Application No. PCT/IL2013/050180.
Int'l Search Report issued Jul. 31, 2103 in Int'l Application No. PCT/IL2013/050313.
Int'l Search Report issued Jul. 26, 2013 in Int'l Application No. PCT/IL2013/050316.
English translation of an Office Action issued Jun. 19, 2013 in JP Application No. 2012-531551.
Office Action issued Aug. 20, 2013 in U.S. Appl. No. 13/576,461 by Lev.
Int'l Preliminary Report on Patentability issued Aug. 28, 2012 in Int'l Application No. PCT/IL2011/000186.
Office Action issued Mar. 1, 2012 in JP Application No. 2007-510229.
Int'l Search Report issued Mar. 7, 2012 in Int'l Application No. PCT/IL2011/000829; Written Opinion.
Office Action issued Mar. 13, 2012 in CA Application No. 2,563,643.
Office Action issued Mar. 1, 2012 in CN Application No. 2008801108283.4.
Office Action issued Mar. 6, 2012 in U.S. Appl. No. 12/678,928.
Int'l Search Report issued Feb. 3, 2011 in Int'l Application No. PCT/IL2010/000777; Written Opinion.
Int'l Search Report issued Mar. 17, 2011 in Int'l Application No. PCT/IL2010/000854; Written Opinion.
Int'l Search Report issued Mar. 17, 2011 in Int'l Application No. PCT/IL2010/000915; Written Opinion.
U.S. Appl. No. 13/505,790 by Lev, filed May 3, 2012.
U.S. Appl. No. 13/505,881 by Lev, filed May 3, 2012.
U.S. Appl. No. 13/576,461 by Lev, filed Aug. 1, 2012.
Office Action issued Jun. 14, 2012 in U.S. Appl. No. 29/376,980.
Office Action issued Jun. 15, 2012 in U.S. Appl. No. 29/413,170.
Office Action issued Jun. 21, 2012 in U.S. Appl. No. 12/596,167.
Int'l Search Report issued Aug. 16, 2012 in Int'l Application No. PCT/IL2012/000164.
International Search Report Issued Jan. 23, 2007 in Int'l Application No. PCT/IL/2006/001228.
IV disposables sets catalogue, Cardinal Health, Alaris® products, SmartSite® access devices and accessories product No. 10013365, SmartSite add-on bag access device with spike adapter and needle-free valve bag access port, pp. 1-5, Fall edition (2007).
Drug Adminsitration Systems product information sheets; http://www.westpharma.com/eu/en/products/Pages/Vial2Bag.aspx; pp. 1-3 (admitted prior art).
Office Action Issued Jun. 8, 2010 in U.S. Appl. No. 12/112,490 by Zinger.
Office Action issued Sep. 28, 2010 in U.S. Appl. No. 12/112,490 by Zinger.
Article with picture of West Pharmaceutical Services' Vial2Bag Needleless System, [on-line]; ISIPS Newsletter, Oct. 26, 2007]; retrieved from Internet Feb. 16, 2010]; URL:<http://www.isips.org/reports/ISIPS_Newsletter_October_26_2007. html.> (7 pages. see pp. 5-6).
Office Action issued Jun. 15, 2011 in JP Application No. 2008-538492.
Translation of Office Action issued Jun. 18, 2012 in JP Application No. 2008-538492.
Translation of Office Action issued Apr. 15, 2013 in JP Application No. 2008-538492.
Office Action issued Jul. 13, 2012 in U.S. Appl. No. 12/112,490 by Zinger.
Office Action issued Jan. 23, 2013 in U.S. Appl. No. 12/112,490 by Zinger.
Int'l Preliminary Report on Patentability issued May 6, 2008 in Int'l Application No. PCT/IL2006/001228.
Int'l Search Report & Written Opinion issued on Mar. 7, 2012 in Int'l Application No. PCT/IL2011/000829.
U.S. Appl. No. 13/884,981 by Denenburg, filed May 13, 2013.
Office Action issued May 31, 2013 in U.S. Appl. No. 13/505,790.
Int'l Search Report issued Jun. 19, 2013 in Int'l Application No. PCT/IL2013/050167.
U.S. Appl. No. 14/005,751 by Denenburg, filed Sep. 17, 2013.
English translation of an Office Action issued Jul. 26, 2013 in JP Application No. 2012-538464.
U.S. Appl. No. 29/438,134 by Lev, filed Nov. 27, 2012.
U.S. Appl. No. 29/438,141 by Gilboa, filed Nov. 27, 2012.
English translation of an Office Action issued Sep. 10, 2013 in JP Application No. 2012-554468.
Office Action issued Nov. 11, 2013 in IL Application No. 218730.
U.S. Appl. No. 29/478,723 by Lev, filed Jan. 8, 2014.
U.S. Appl. No. 29/478,726 by Lev, filed Jan. 8, 2014.
Office Action issued Jan. 2, 2014 in U.S. Appl. No. 13/505,881 by Lev.

FLUID TRANSFER ASSEMBLY WITH VENTING ARRANGEMENT

CROSS-REFERENCE TO RELATED APPLICATION

This application is a Section 371 of International Application No. PCT/IL2011/000186, filed Feb. 23, 2011, which was published in the English language on Sep. 1, 2011, under International Publication No. WO 2011/104711 A1, and the disclosure of which is incorporated herein by reference.

FIELD OF THE INVENTION

The invention relates to fluid transfer assemblies for liquid drug reconstitution and administration.

BACKGROUND OF THE INVENTION

Commonly owned U.S. Pat. No. 6,558,365 to Zinger et al. illustrates and describes a fluid transfer assembly including a pair of initially inter-engaged vial adapters for use with a pair of vials for liquid drug reconstitution and administration purposes. Such fluid transfer assemblies are commercially available under the registered trademark MIX2VIAL® from the present Applicant Medimop Medical Projects Ltd., Ra'anana, Israel. The pair of vial adapters includes a vial adapter including a female connector referred to hereinafter as a "female vial adapter" and another vial adapter including a male connector referred to hereinafter as a "male vial adapter". The male and female connectors are Luer connectors and preferably Luer lock connectors. The vials typically include one vial containing diluent and another vial containing a powdered drug medicament under vacuum. Typical vial sizes include 13 mm neck diameter and 20 mm neck diameter.

Liquid drug reconstitution and administration starting from an initial assembled configuration of a fluid transfer assembly includes the steps of:

(a) holding the diluent containing vial on a flat surface and downwardly snap fitting the male vial adapter thereonto;

(b) inverting the fluid transfer assembly to hold the fluid transfer assembly upright with the male vial adapter and its connected diluent containing vial above the female vial adapter;

(c) holding the medicament containing vial on a flat surface and downwardly snap fitting the female vial adapter thereonto whereupon the prevailing vacuum in the medicament containing vial rapidly draws the diluent from the diluent containing vial thereinto to form a reconstituted liquid drug and leaves a residual vacuum in the sealed assemblage of the fluid transfer assembly and two connected vials;

(d) gently agitating the sealed assemblage of the fluid transfer assembly and the two connected vials to fully reconstitute the liquid drug medicament in the vial connected to the female vial adapter;

(e) detaching the male vial adapter from the female vial adapter by unscrewing the male Luer lock connector from the female Luer connector;

(f) screw threading a syringe with a male Luer lock connector onto the female vial adapter;

(g) inverting the female vial adapter and its connected vial for aspirating the reconstituted liquid drug into the syringe; and (h) unscrewing the syringe from the female vial adapter, attaching a needleand administering the reconstituted liquid drug.

Steps (a) to (d) are performed under sterile conditions but step (e) draws ambient air into the vial connected to the female vial adapter via its female connector to equalize the negative pressure therein. Ambient air particularly in outpatient clinics, hospitals, and the like, may be septic and therefore contaminate reconstituted liquid drug contents. Moreover, in some circumstances, female vial adapters are prepared in advance of immediate use and left standing for subsequent use thereby leaving their reconstituted liquid drug contents exposed to ambient air.

SUMMARY OF THE INVENTION

The present invention is directed toward fluid transfer assemblies similar in construction and operation as the hitherto described fluid transfer assemblies and additionally provisioned for precluding undesirable drawing of potentially septic air into a vial connected to a female vial adapter on detaching a male vial adapter therefrom thereby maintaining the sterility of a reconstituted liquid drug. This is achieved by replacing a hitherto employed non-vented female vial adapter by a vented female vial adapter including a venting arrangement having an air filter and one or more vent ports and providing an otherwise conventional male vial adapter with a sealing arrangement having one or more port sealing members for sealing the vent ports.

The present invention is designed such that the aforesaid step e) detaching the male vial adapter from the female vial adapter is effectively divided into a two step process undiscernable to a user as follows: First, initial axial displacement causes the sealing arrangement to open a female vial adapter's vent ports for drawing ambient air into its connected vial containing a reconstituted liquid drug through its air filter to equalize its residual vacuum with ambient pressure prior to the male connector unsealing the female connector. The air filter precludes septic air being drawn into a reconstituted liquid drug containing vial thereby maintaining the sterility of its contents. And second, continued axial displacement to complete the mechanical detachment of the male vial adapter from the female vial adapter.

The fluid transfer assemblies of the present invention are preferably blister packed with their male vial adapters preassembled on their female vial adapters thereby expediting their use for reconstitution and administration purposes. Alternatively, a male vial adapter and a female vial adapter can be supplied as discrete components requiring a user to assembly the male vial adapter on the female vial adapter prior to reconstitution and administration purposes. Fluid transfer assemblies can be pre-assembled in a ready for reconstitution state, namely, their male connectors seal their female connectors and their sealing arrangements seal their venting arrangements. Alternatively, fluid transfer assemblies can be pre-assembled in a non ready for reconstitution state with their sealing arrangements axially displaced from their vent ports and therefore not sealing their venting arrangements. Such fluid transfer assemblies require axial displacement of their male vial adapter toward their female vial adapter for urging their male connectors to seal their female connectors and their sealing arrangements to seal their venting arrangements thereby priming the fluid transfer assemblies from their non ready for reconstitution state to their ready for reconstitution state. Such axial displacement preferable automatically occurs during the snap fit of a fluid transfer assembly on its vials for reconstitution purposes. The latter non ready for reconstitution state is envisaged to afford a longer shelf life than the former ready for reconstitution state by virtue of the sealing arrangement only sealing the venting arrangement as required for reconstitution purposes and thereby precluding inadvertent adhesion therebetween.

The present invention can be readily implemented for use with a wide range of vials including inter alia 13 mm neck diameter vials, 20 mm neck diameter vials and so-called large diameter vials with typically 28 mm, 32 mm and larger neck diameter. The one or more port sealing members are preferably designed to additionally stabilize a male vial adapter on a vented female vial adapter as well as sealing the latter's one or more vent ports. Fluid transfer assemblies intended for use with large diameter large vials preferably include a vented female vial adapter having a female connector adapted to receive an IV spike. Fluid transfer assemblies can include alternative inter-engagement arrangements to a screw threading arrangement including inter alia friction fit arrangements, and the like.

The female vial adapter can be optionally provided with a closure for sealing its female connector for maintaining a sterile environment for its reconstituted liquid drug contents subsequent to mechanical detachment of the male vial adapter from the female vial adapter. The closure can be in the form of a manually placed cap, a pre-split septum, and the like.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF PREFERRED EMBODIMENTS OF THE INVENTION

Figure 1:
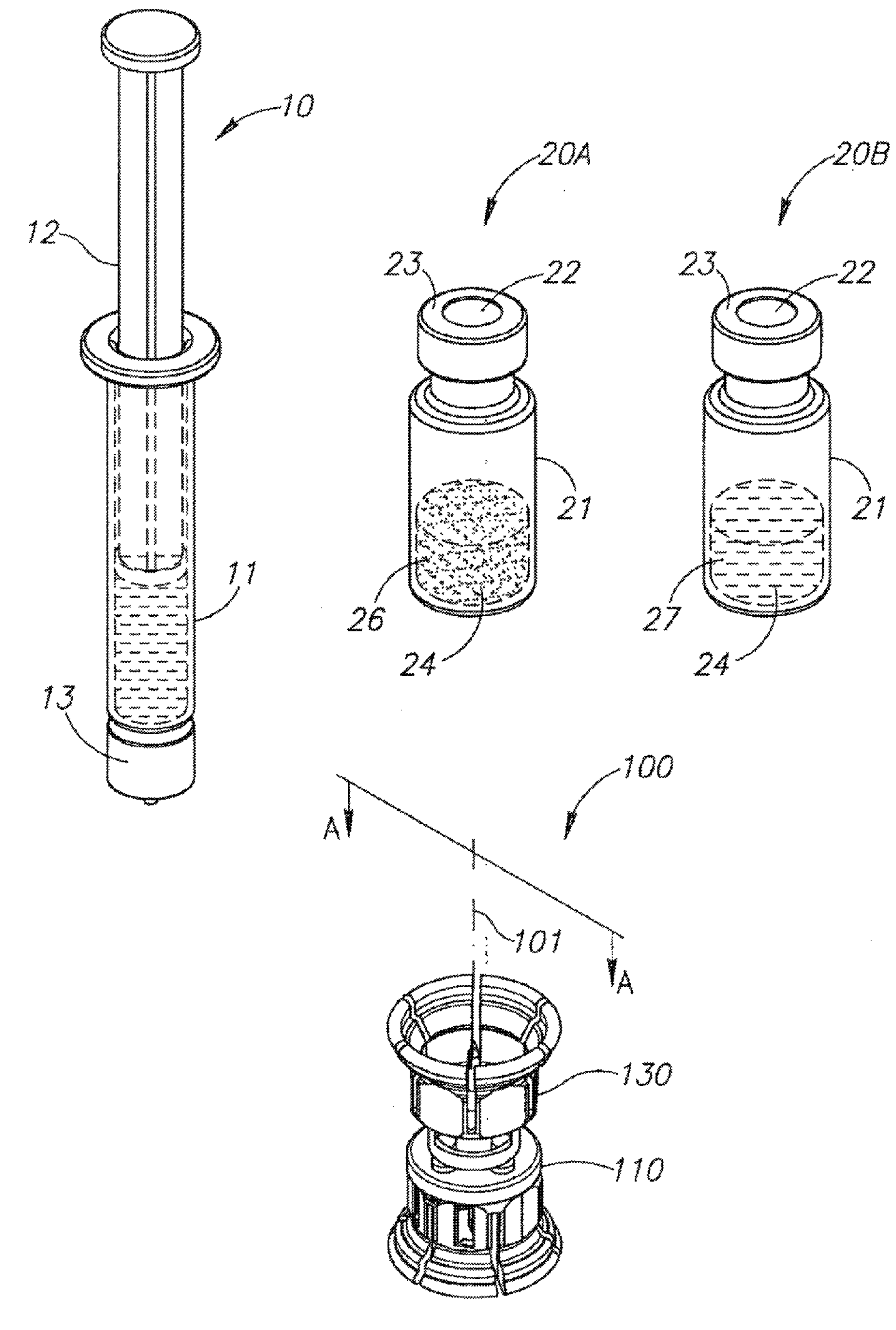
FIG. 1 is a pictorial representation of a fluid transfer assembly in an initial ready for reconstitution state in accordance with a first embodiment of the present invention, a syringe and pair of vials, the fluid transfer assembly including a vented female vial adapter and a male vial adapter.

FIG. 1 shows a fluid transfer assembly 100 in an initial ready for reconstitution state for use with an empty syringe 10 and a pair of vials 20A and 20B constituting medicinal vessels. The fluid transfer assembly 100 has a longitudinal axis 101 and includes a vented female vial adapter 110 having a venting arrangement 110A and initially screw threaded on a male vial adapter 130 having a sealing arrangement 130A for selectively sealing the venting, arrangement 110A. The syringe 10 includes a barrel 11 with a plunger 12 and a male Luer lock connector 13. The syringe 10 can be formed with other types of male connectors. The vials 20 include an open topped bottle 21 sealed by a vial stopper 22 capped by a metal band 23. The vial 20A has a vial interior 24 containing either a powder or liquid medicament 26 under negative pressure. The vial 20B has a vial interior 24 containing a liquid medicament 27 for reconstituting the vial contents 26 to form reconstituted liquid drug contents 28. The liquid medicament 27 can be diluent or containing an active drug component.

Figure 2:
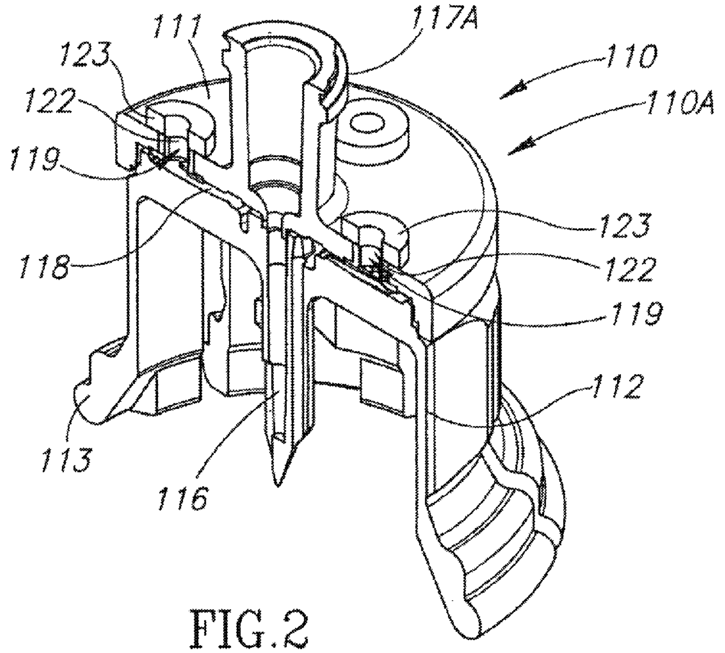
FIG. 2 is a top perspective cutaway view of FIG. 1's vented female vial adapter along line A-A in FIG. 1.
Figure 3:
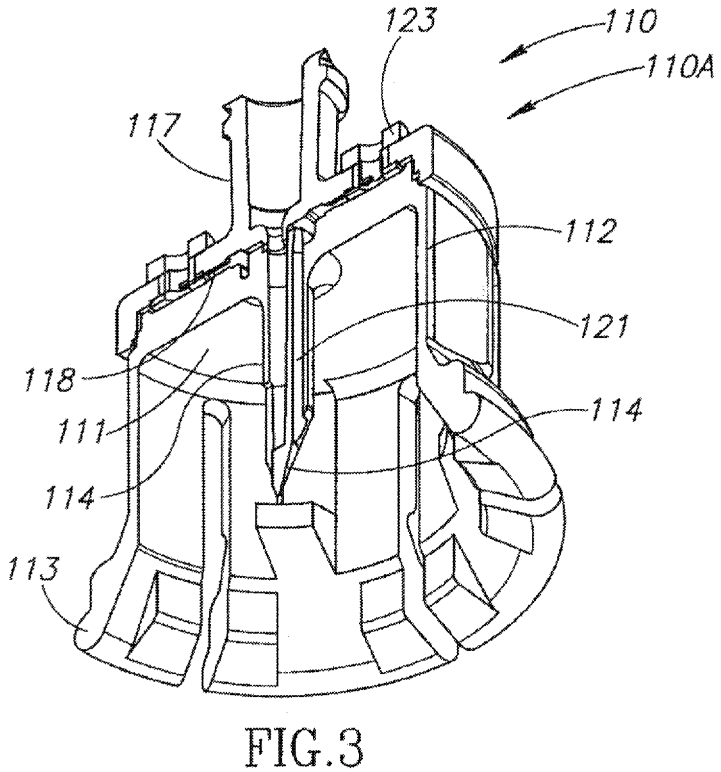
FIG. 3 is a bottom perspective cutaway view of FIG. 1's vented female vial adapter.

FIGS. 2 and 3 show the vented female vial adapter 110 includes a transverse top wall 111, a downward depending skirt 112 with flexing members 113 for snap fitting onto the vial 20A, and a downward depending pointed cannula 114 having a liquid transfer lumen 116 for puncturing the vial 20A's vial stopper 22, and an oppositely directed female connector 117 in flow communication with the liquid transfer lumen 116. The female connector 117 is preferably a female Luer connector including an external screw thread 117A at its free end.

The venting arrangement 110A includes an annular air filter 118 disposed beneath the top wall 111, four equi-spaced circular vent ports 119 formed in the top wall 111 and a venting lumen 121 formed in the pointed cannula 114 for establishing flow communication between the vent ports 119 and the vial 20A's vial interior on snap fitting the female vial adapter 110 on the vial 20A. The vent ports 119 are flush with the top wall 111 and each include a vent aperture 122 and an annular elastomer rim 123 disposed on the top wall 111 for sealing same on application of an axial force thereon.

Figure 4:
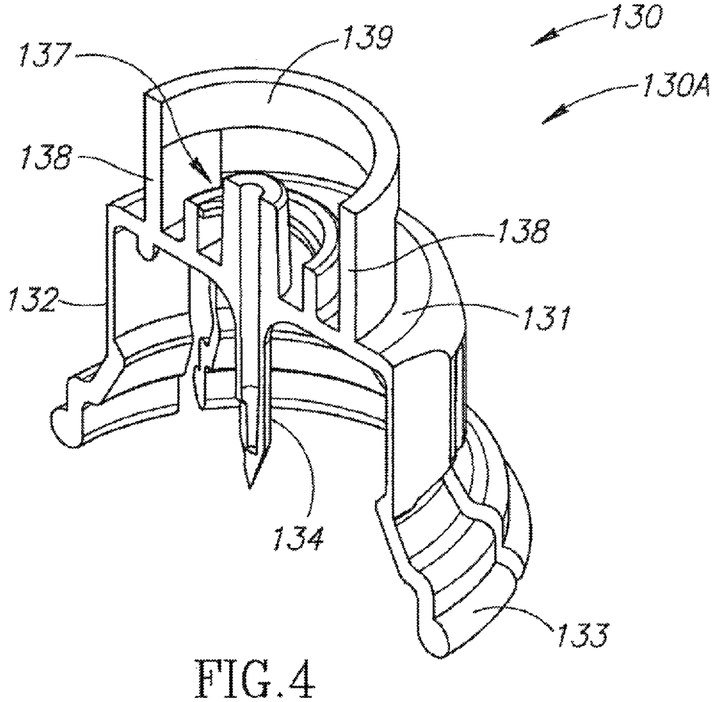
FIG. 4 is a longitudinal cross section of FIG. 1's male vial adapter.
Figure 5:
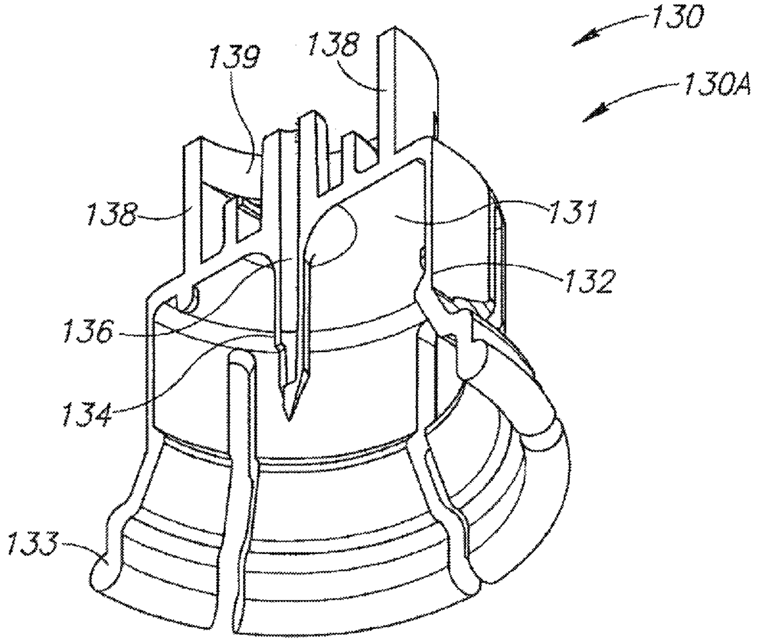
FIG. 5 is a bottom perspective cutaway view of FIG. 1's vented female vial adapter.

FIGS. 4 and 5 show the male vial adapter 130 includes a transverse top wall 131, a downward depending skirt 132 with flexing members 133 for snap fitting onto the vial 20B, a downward depending pointed cannula 134 with a liquid transfer lumen 136 for puncturing the vial 20B's vial stopper 22 and an oppositely directed male connector 137 in flow communication with the liquid transfer lumen 136. The male, connector 137 is preferably a male Luer lock connector for screw threading engagement with the female Luer connector 117.

The sealing arrangement 130A includes a pair of opposite axial directed port sealing members 138 for supporting an annular port sealing member 139 for applying an axial force on the elastomer rims 123 for sealing the vent ports 119 in the initial ready for reconstitution state of the fluid transfer assembly 100. The sealing arrangement 130A also stabilizes the male vial adapter 130 on the vented female vial adapter 110 in the fluid transfer assembly 100's initial ready for reconstitution state.

FIGS. 6 to 9 show use of the fluid transfer assembly 100 for reconstitution and administration purposes.

Figure 6:
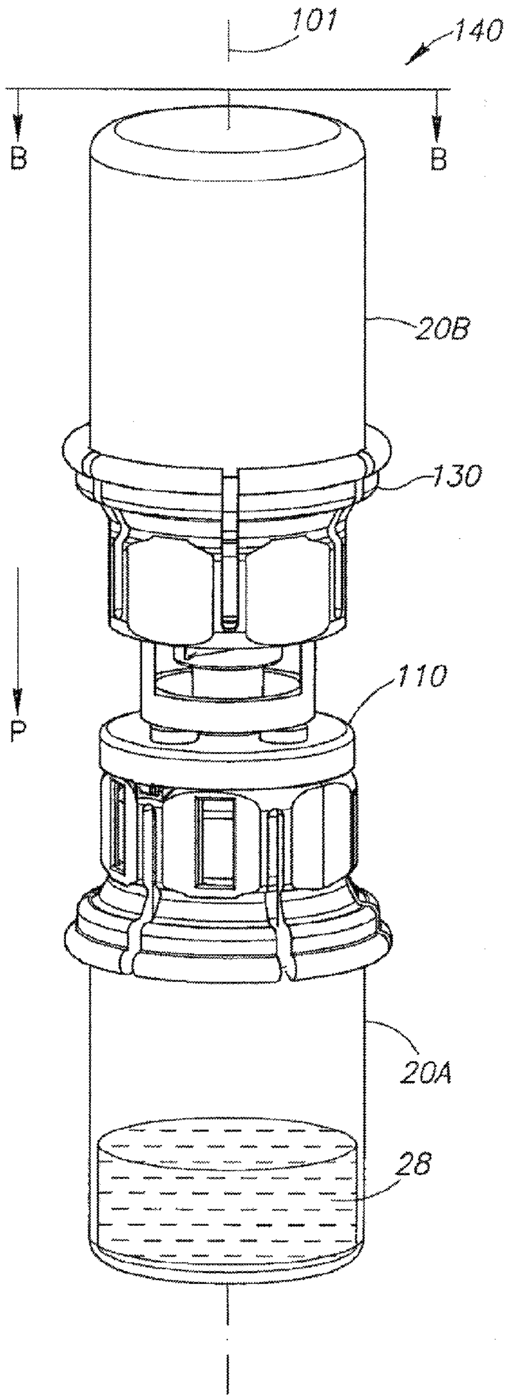
FIG. 6 is a front perspective view of an assemblage of FIG. 1's fluid transfer assembly and two connected vials for reconstitution of liquid drug contents.
Figure 7:
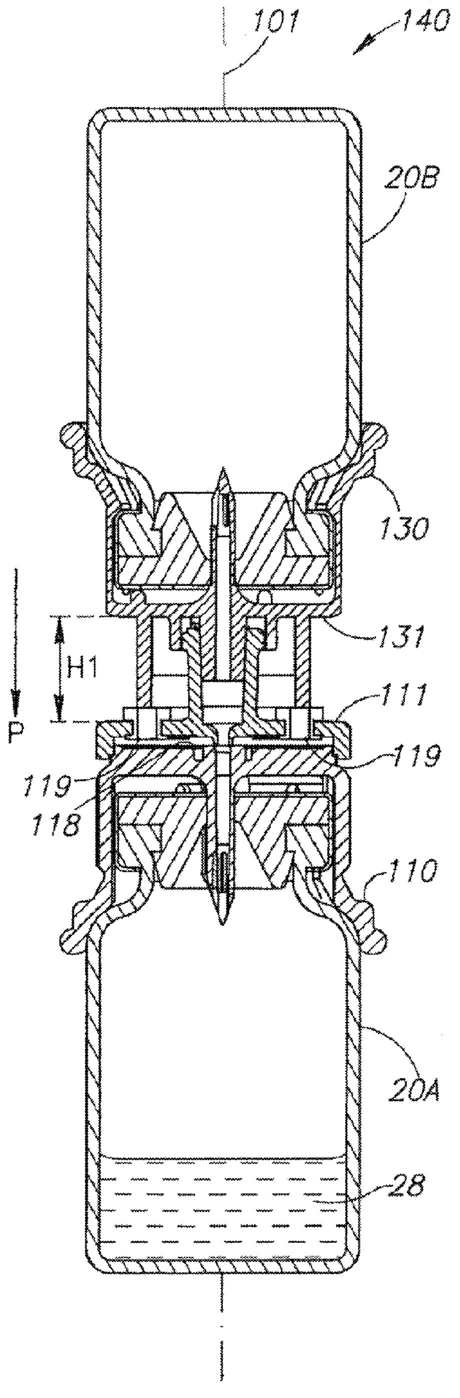
FIG. 7 is a longitudinal cross section of a FIG. 6's assemblage along line B-B therein.

FIGS. 6 and 7 show an assemblage 140 of the fluid transfer assembly 100 snap fitted on the two vials 20A and 20B on following the aforesaid steps (a) to (d) to form reconstituted liquid drug contents 28 in the vial 20A. The assemblage 140 includes the female connector 117 in sealed engagement with the male connector 137 and the sealing arrangement 130A sealing the vent ports 119 prior to snap fitting the fluid transfer assembly 100 on the vials 20A and 20B. The axial separation between the opposite top walls 111 and 131 is denoted by the height H1. The arrow P denotes drawing of the liquid medicament 27 from the vial 20B into the vial 20A to form the reconstituted liquid drug contents 28.

Figure 8:
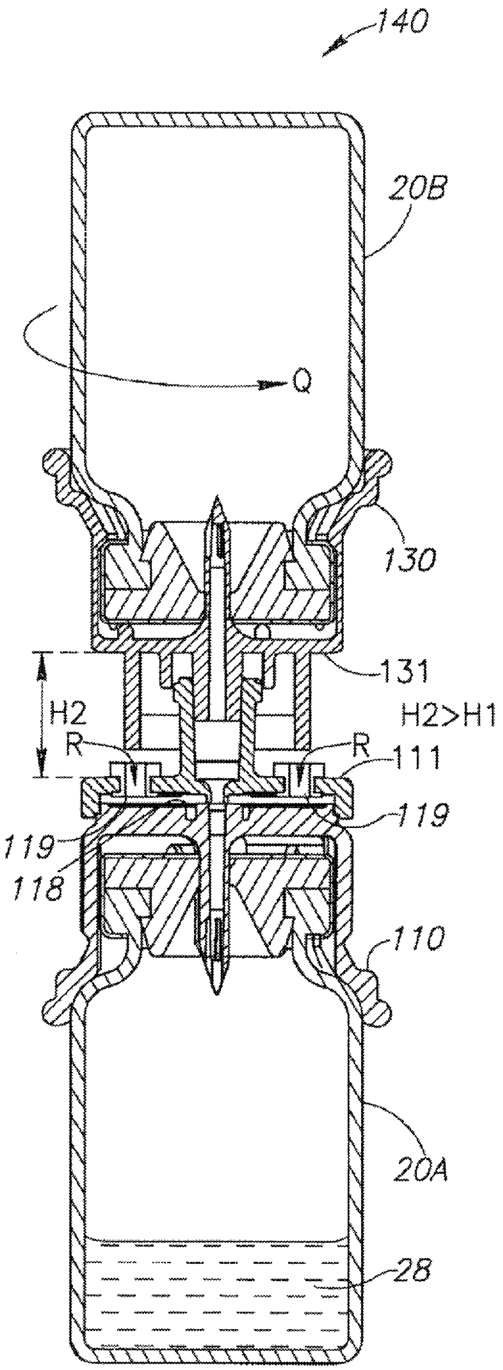
FIG. 8 is a longitudinal cross section of a FIG. 6's assemblage along line B-B therein subsequent to initial axial displacement of the male vial adapter from the vented female vial adapter.

FIG. 8 shows an initial axial displacement of the male vial adapter 130 from the vented female vial adapter 110 by initial unscrewing the male Luer lock connector 137 from the female Luer connector 117 denoted by arrow Q. The initial axial displacement is denoted by the axial separation H2 where H2 is slightly greater than H1 and is designed to enable the sealing arrangement 130A to open the vent ports 119 before the male Luer lock connector 137 unseals the female Luer connector 117. The initial axial displacement is typically in the order of the pitch of the Luer lock inter-engagement between the male Luer lock connector 137 and the female lock connector 117. The opening of the venting arrangement 110A draws filtered air through the air filter 118 into the vial 20A as denoted by arrows R to equalize its residual negative pressure with ambient pressure.

Figure 9:
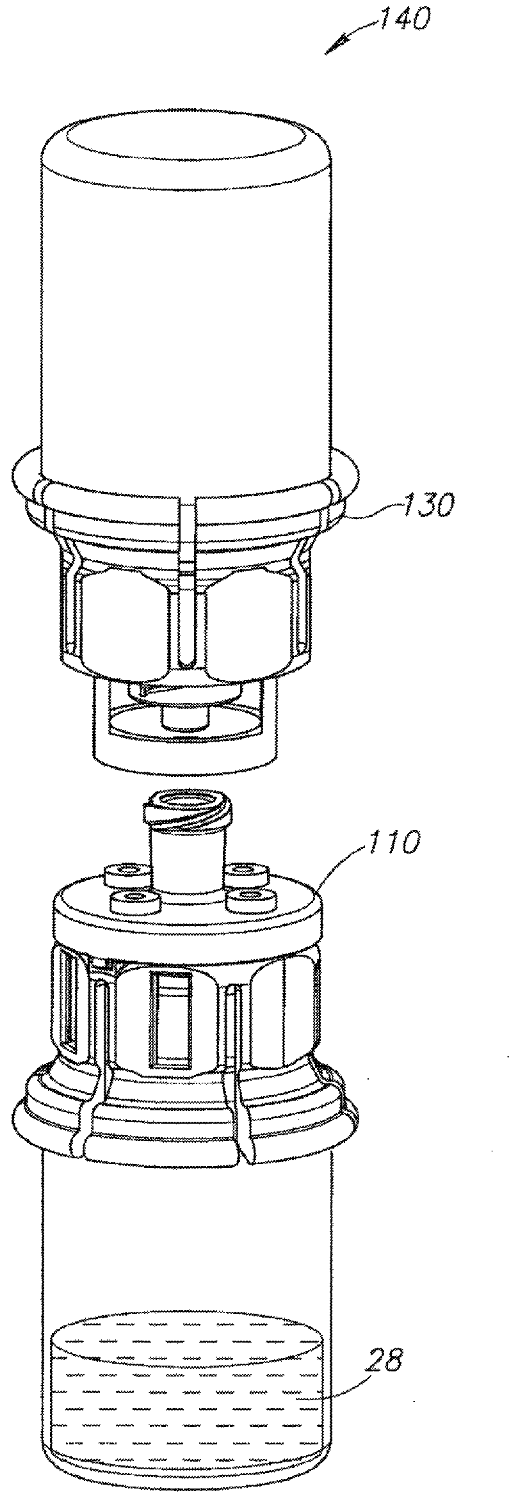
FIG. 9 is a front perspective view of FIG. 6's assemblage subsequent to complete mechanical detachment of the male vial adapter from the vented female vial adapter.

FIG. 9 shows continued axial displacement of the male vial adapter 130 from the vented female vial adapter 110 by continuing unscrewing the male Luer lock connector 137 from the female Luer connector 117 until complete mechanical detachment thereby exposing the female Luer connector 117 for attachment of the syringe 10 for administration of reconstituted liquid drug contents 27.

Figure 10:
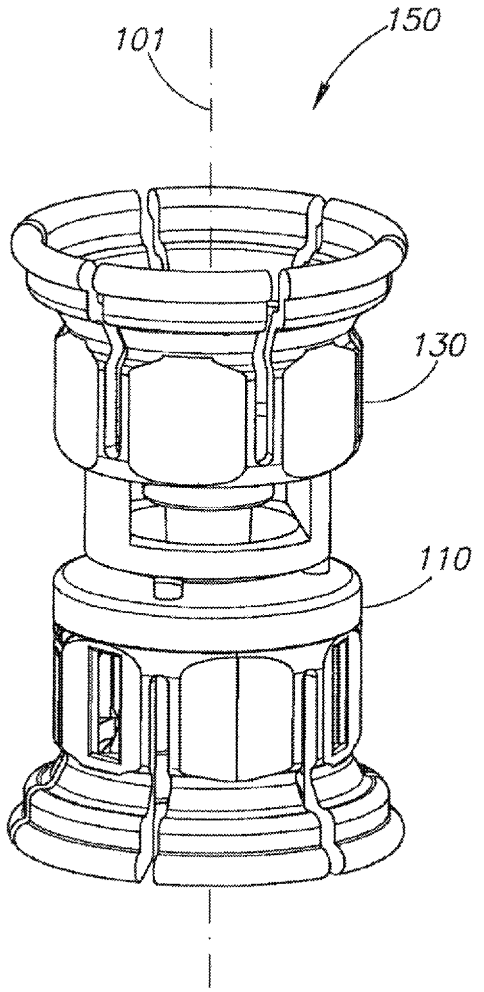
FIG. 10 is a pictorial representation of a fluid transfer assembly in an initial ready for reconstitution state in accordance with a second embodiment of the present invention.
Figure 11:
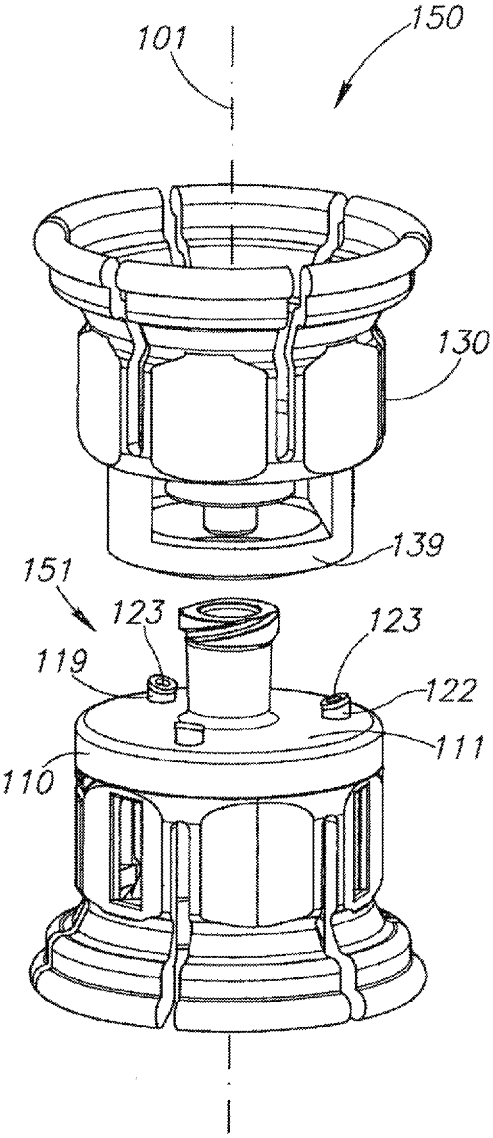
FIG. 11 is a pictorial representation of FIG. 10's vented female vial adapter and male vial adapter.

FIGS. 10 and 11 show a fluid transfer assembly 150 similar in construction and operation as the fluid transfer assembly 100 and therefore similar parts are likewise numbered. The former 150 includes a vented female vial adapter 110 with a venting arrangement 151 modified with respect to the venting arrangement 110A. The venting arrangement 151 includes open topped vent ports 119 raised with respect to the top wall 111 and each having a vent aperture 122 inclined towards the longitudinal axis 101. The vent ports 119 are provided with annular elastomer rims 123 for sealing same on depression by an annular port sealing member 139 in an initial ready for reconstitution state of the fluid transfer assembly 150.

Figure 12:
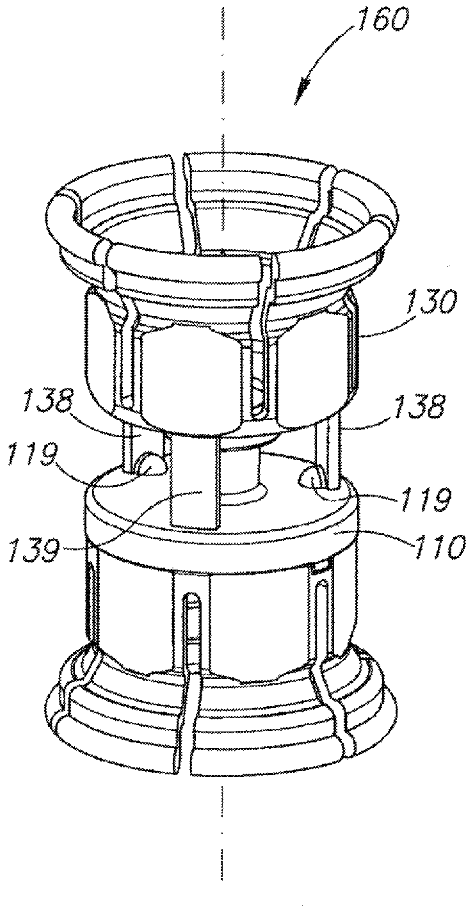
FIG. 12 is a pictorial representation of a fluid transfer assembly in an initial ready for reconstitution state in accordance with a third embodiment of the present invention.
Figure 13:
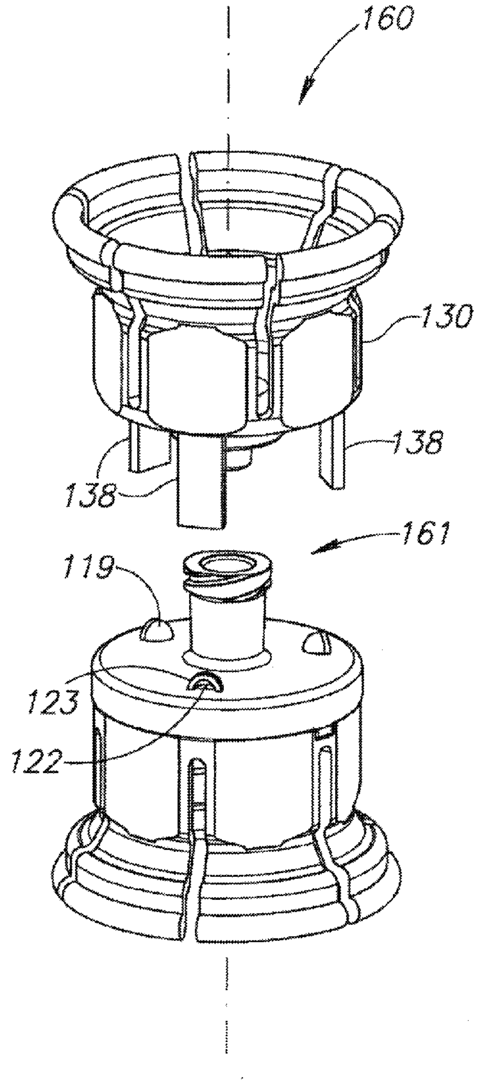
FIG. 13 is a pictorial representation of FIG. 12's vented female vial adapter and male vial adapter.

FIGS. 12 and 13 show a fluid transfer assembly 160 similar in construction and operation as the fluid transfer assembly 100 and therefore similar parts are likewise numbered. The former 160 includes a vented female vial adapter 110 with a venting arrangement 161 modified with respect to the venting arrangement 110A. The venting arrangement 161 includes quarter sphere shaped vent ports 119 raised with respect to the top wall 111 and each having a vent aperture 122 facing radial outward with respect to the longitudinal axis 101 and fitted with a semi-circular elastomer rim 123. The male vial adapter 130 has three elongated port sealing members 139 for sealing the vent ports 119 in an initial ready for reconstitution state of the fluid transfer assembly 160.

Figure 14:
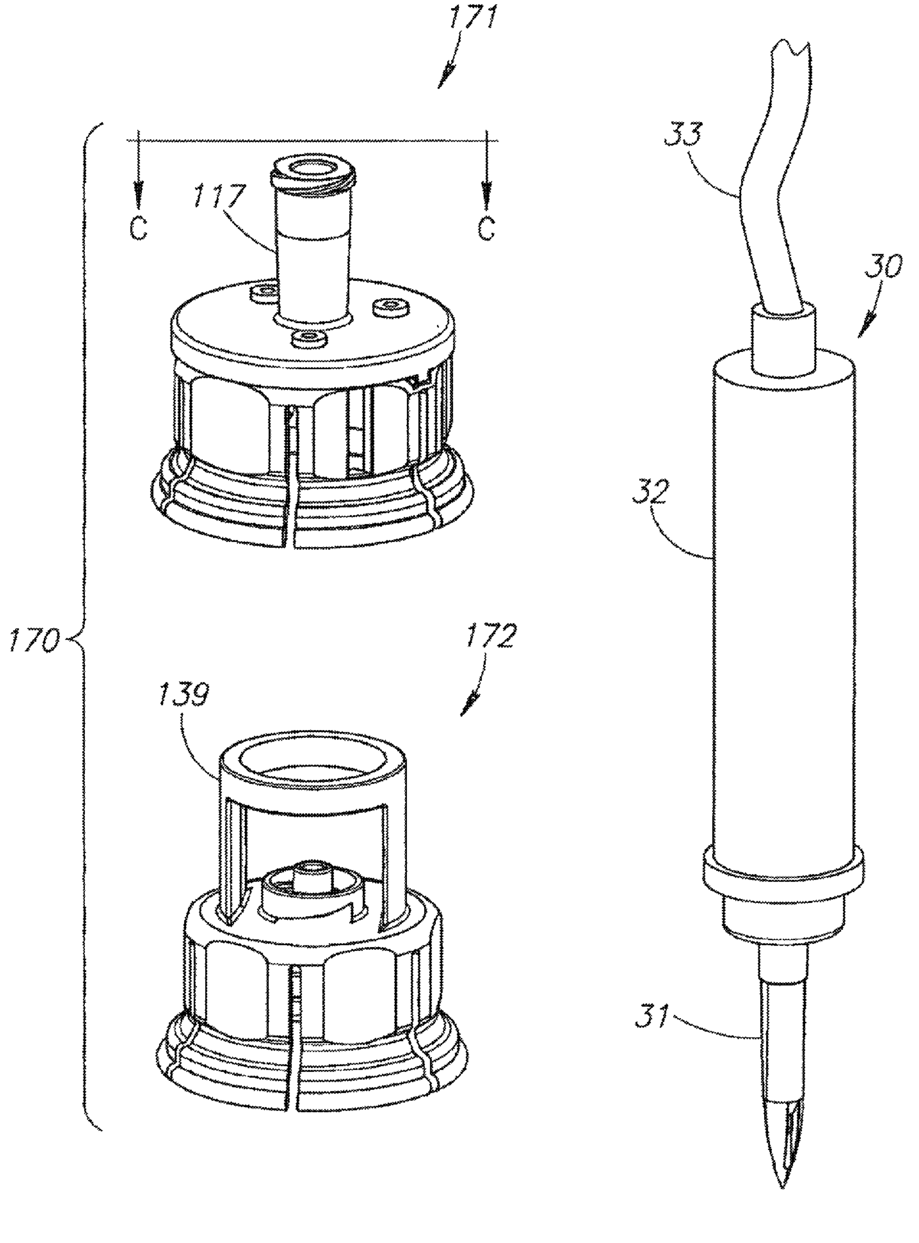
FIG. 14 is a pictorial representation of a fluid transfer assembly in accordance with a fourth embodiment of the present invention for use with large diameter vials and an IV spike.

FIG. 14 shows a fluid transfer assembly 170 for use with a pair of large diameter vials, for example 32 mm neck diameter, and an IV device 30 including an IV spike 31, a chamber 32, and IV tubing 33. The fluid transfer assembly 170 has a similar construction to the fluid transfer assembly 100 and therefore similar parts are likewise numbered. The fluid transfer assembly 170 includes a vented female vial adapter 171 including a venting arrangement 110A and a male vial adapter 172 including a sealing arrangement 130A. The fluid transfer assembly 170 has an initial ready for reconstitution state with the male vial adapter 172 screw thread engaged on the female vial adapter 171.

Figure 15:
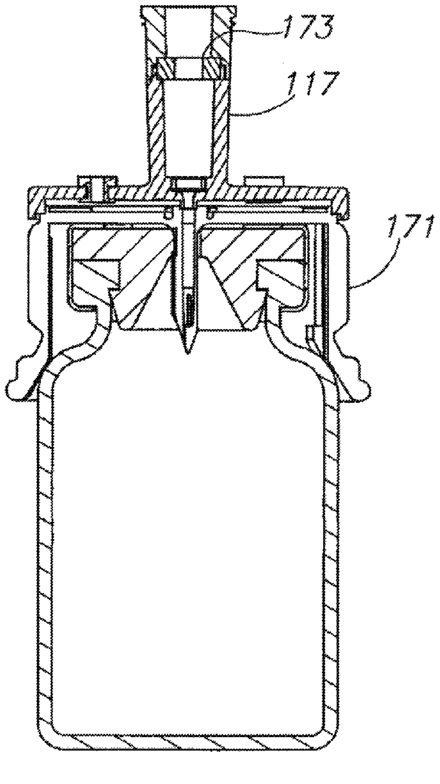
FIG. 15 is a longitudinal cross section of FIG. 14's vented female vial connector along line C-C therein.
Figure 16:
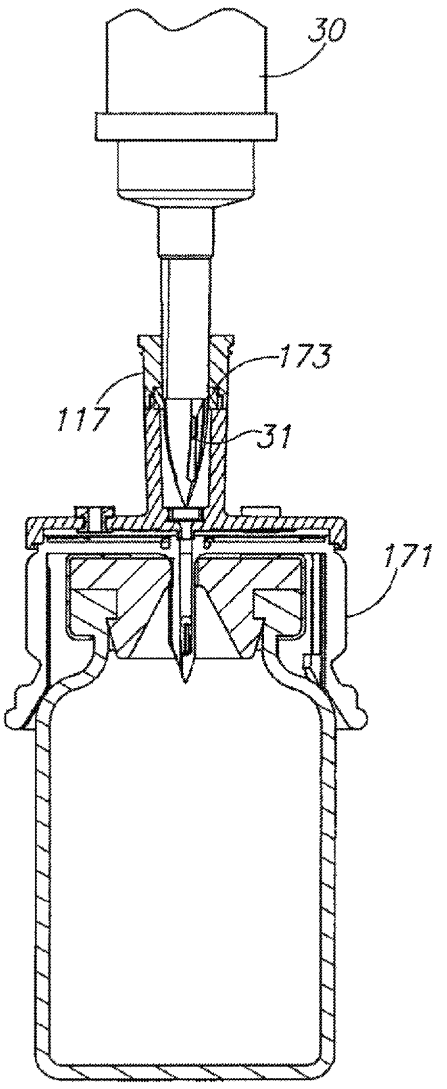
FIG. 16 is a longitudinal cross section of FIG. 14's vented female vial connector with an IV spike for liquid drug administration.

The vented female vial adapter 171 differs from the vented female vial adapter 110 insofar its female connector 117 is fashioned for receiving the IV spike 31. The female vial adapter 171 includes a female connector 117 which is taller with respect to its top wall 111 than the female vial adapter 110's female connector 117 to sealingly accommodate the IV spike 31. The male vial adapter 172 includes a port sealing member 139 which is taller with respect to its top wall 131 than the male vial adapter 130's port sealing member 139 to compensate for the female vial adapter 171's female connector 117. FIGS. 15 and 16 show the female connector 117 includes an annular seal 173 for sealing a male connector 137 in an initial ready for reconstitution state of the fluid transfer assembly 170 and an IV spike 31 during liquid drug administration.

Figure 17:
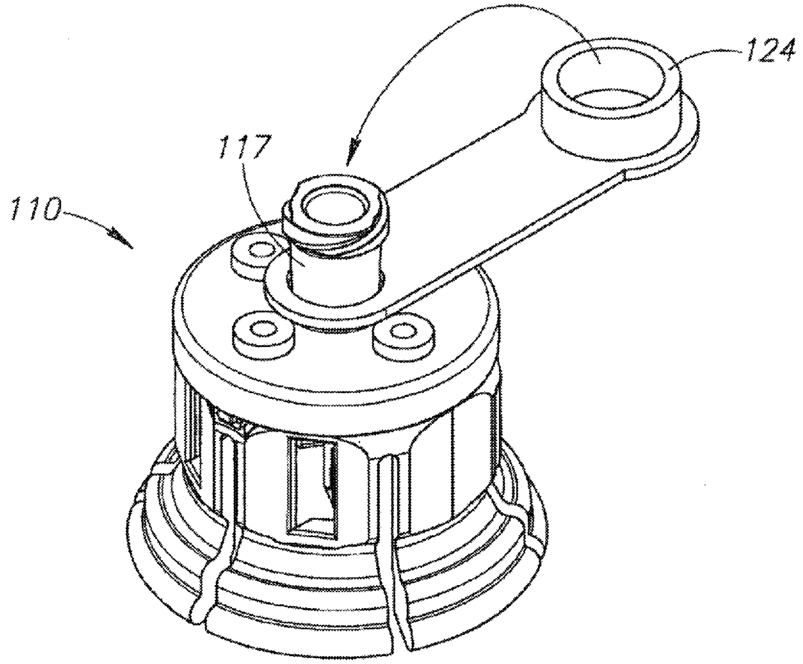
FIG. 17 is a pictorial representation of FIG. 1's vented female vial adapter including a manually placed cap for sealing its female connector.
Figure 18:
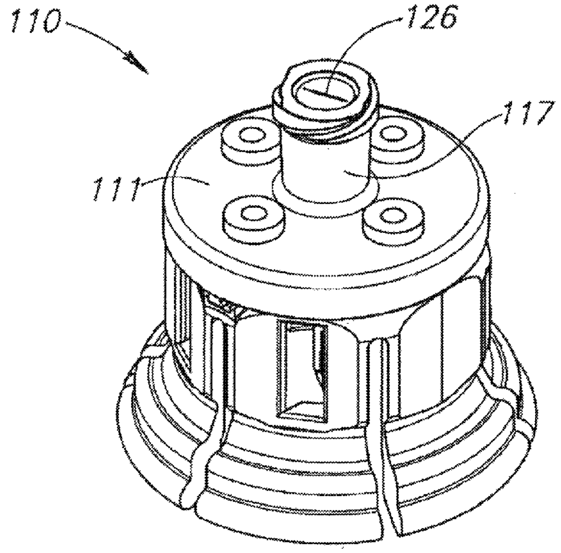
FIG. 18 is a top perspective cutaway view of FIG. 1's vented female vial adapter along line A-A in FIG. 1 including a pre-split septum for sealing its female connector.

FIG. 17 shows FIG. 1's vented female vial adapter 110 including a manually placed cap 124 for sealing its female connector 117 subsequent to reconstitution of liquid drug contents for maintaining sterile conditions while the female vial adapter 110 is left standing for subsequent use. Alternatively, FIG. 18 shows FIG. 1's vented female vial adapter 110 with a pre-split septum 126 for the same purpose.

Figure 19:
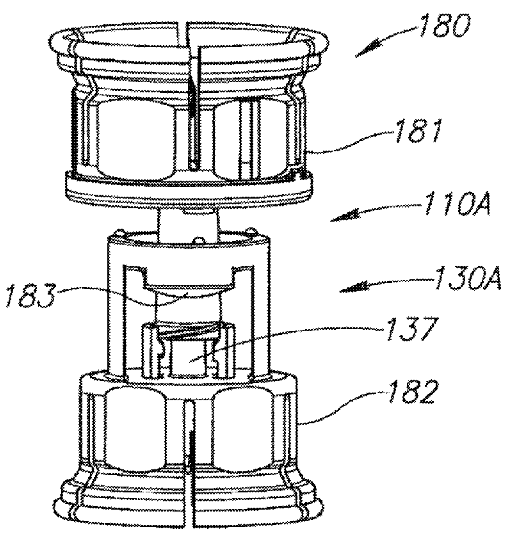
FIG. 19 is a pictorial representation of a fluid transfer assembly in an initial non ready for reconstitution state, the fluid transfer assembly including a vented female vial adapter and a male vial adapter.

FIG. 19 shows a fluid transfer assembly 180 similar in construction to the fluid transfer assembly 100 but differing therefrom insofar it has an initial non ready for reconstitution state as opposed to an initial ready for reconstitution state. The fluid transfer assembly 180 includes a female vial adapter 181 having a venting arrangement 110A and a female connector 117 and a male vial adapter 182 having a sealing arrangement 130A and a male connector 137. The female vial adapter 181 can be constituted by either a female vial adapter 110 for use with syringes 10 for administration purposes or a female vial adapter 171 for use with IV devices 30 for administration purposes. The male vial adapter 182 correspondingly includes a suitably shaped and dimensioned male connector 137. The difference between the non ready for reconstitution state and the ready for reconstitution state is that in the former state the male vial adapter 182 is axially displaced from the female vial adapter 181 such that the male connector 137 does not seal the female connector 117 and the sealing arrangement 130A does not seal the venting arrangement 110A.

Figure 20:
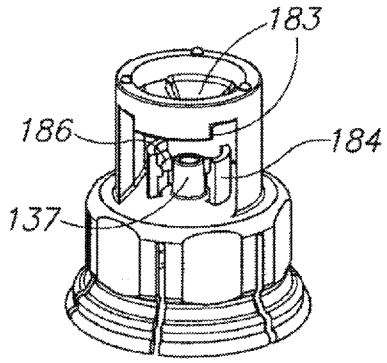
FIG. 20 is a pictorial representation of FIG. 19's male vial adapter.

FIG. 20 shows the male vial adapter 182 is similar to the male vial adapter 130 but differs therefrom in two respects as follows: The sealing arrangement 130A additionally includes a pair of opposite inward directed engagement members 183 for engaging a female connector 117 in the initial non ready for reconstitution state for assembling the male vial adapter 182 on the female vial adapter 181. Also, the male vial adapter 182 includes three equispaced axial directed grip members 184 lateral to the male connector 137 and having inward directed projections 186 for engaging the female connector's external screw thread 117A on axial displacement of the male vial adapter towards the female vial adapter.

Figure 21:
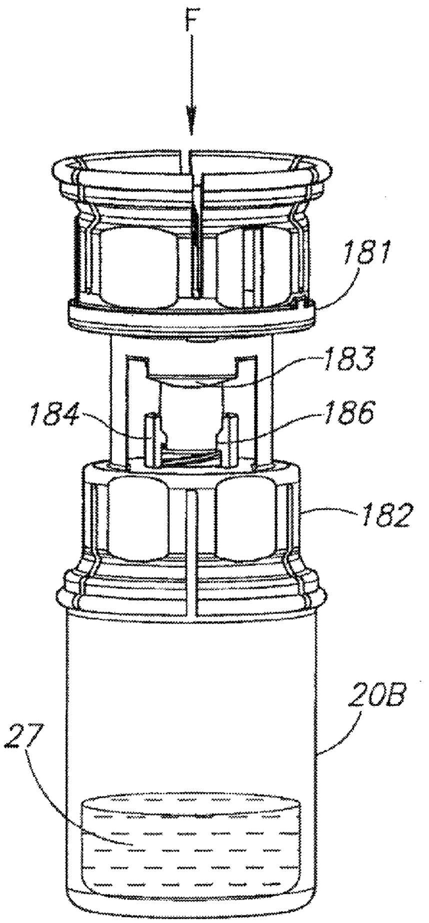
FIG. 21 is a pictorial representation of FIG. 19's fluid transfer assembly in a ready for reconstitution state.

FIG. 21 shows the fluid transfer assembly 180 pursuant to snap fitting the male vial adapter 182 on a vial 20B containing a liquid medicament 27. A user applies a downward force F on the female vial adapter 181 causing the female vial adapter 181 to axially move towards the male vial adapter 182. The axial displacement causes the sealing arrangement 130A to seal the vent ports 119A and the male connector 137 to seal the female connector 117 thereby effectively priming the fluid transfer assembly 180 into its ready for reconstitution state. The inward directed projections 186 engage the external screw thread 117A in a similar manner to a male Luer lock connector such that a user unscrews the male vial adapter 182 from the female vial adapter 181 for the initial opening of the venting arrangement 110A to enable drawing in of filtered air and the subsequent complete mechanical detachment of the male vial adapter 182 from the female vial adapter 181.

While the invention has been described with respect to a limited number of embodiments, it will be appreciated that many variations, modifications, and other applications of the invention can be made within the scope of the appended claims.

The invention claimed is:

1. A fluid transfer assembly for use with a first vial and a second vial for liquid drug reconstitution and administration purposes, the first vial having a vial opening and a vial stopper sealing the vial opening and a vial interior containing a liquid medicament, the second vial having a vial opening and a vial stopper sealing the vial opening and a vial interior containing a medicament under negative pressure, the liquid medicament intended to reconstitute the second vial's medicament to form reconstituted liquid drug contents, the fluid transfer assembly having a longitudinal axis and comprising:

(a) a female vial adapter having a top wall, a skirt with flex members for snap fitting onto the second vial, a pointed cannula for puncturing the second vial's vial stopper on snap fitting said female vial adapter on the second vial, said pointed cannula including a liquid transfer lumen for establishing flow communication with the second vial's vial interior, and a female connector in flow communication with said liquid transfer lumen; and (b) a male vial adapter having a top wall, a skirt with flex members for snap fitting onto the first vial, a pointed cannula for puncturing the first vial's vial stopper on snap fitting said male vial adapter on the first vial, said pointed cannula including a liquid transfer lumen for establishing flow communication with the first vial's vial interior, and a male connector in flow communication with said liquid transfer lumen and for sealing said female connector on assembling said male vial adapter on said female vial adapter for reconstitution of the liquid drug contents, wherein said female vial adapter having a venting arrangement including i) an air filter underlying said top wall, ii) at least one vent port formed in said top wall and iii) a venting lumen formed in said pointed cannula for establishing flow communication between said at least one vent port and the second vial's vial interior on snap fitting said female vial adapter on the second vial, and said male vial adapter having a sealing arrangement for sealing said at least one vent port during reconstitution of the liquid drug contents, the arrangement being such that pursuant to initial snap fitting of i) said male vial adapter on the first vial and thereafter ii) said female vial adapter on the second vial, the second vial's negative pressure draws the first vial's liquid medicament thereinto for reconstitution with its medicament for reconstituting the reconstituted liquid drug contents, subsequent axial displacement of said male vial adapter from said female vial adapter initially axially displaces said sealing arrangement from said at least one vent port to open said venting arrangement while said male connector continuously seals said female connector such that the second vial draws filtered air only thereinto to equalize its negative pressure and thereafter completes mechanical detachment of said male vial adapter from said female vial adapter for enabling administration of the reconstituted liquid drug contents.

2. The assembly according to claim 1, wherein said sealing arrangement includes at least one axial directed port sealing member for sealing said at least one vent port during reconstitution of the liquid drug contents.

3. The assembly according to claim 2, wherein said at least one axial directed port sealing member includes an annular port sealing member for simultaneously sealing at least one vent port of said at least one vent port during reconstitution of the liquid drug contents.

4. The assembly according to claim 1, wherein said fluid transfer assembly is pre-assembled in an initial ready for reconstitution state including said male vial adapter assembled on said female vial adapter, said male connector sealing said female connector and said sealing arrangement sealing said at least one vent port.

5. The assembly according to claim 1, wherein said fluid transfer assembly is pre-assembled in an initial non ready for reconstitution state including said male vial adapter assembled on said female vial adapter and said sealing arrangement axially displaced from said at least one vent port thereby not sealing said venting arrangement, said fluid transfer assembly requiring axial displacement of said male vial adapter towards said female vial adapter for urging said male connector to seal said female connector and said sealing arrangement to seal said at least one vent port thereby priming said fluid transfer assembly from said initial non ready for reconstitution state to a ready for reconstitution state.

6. The assembly according to claim 5, wherein said sealing arrangement includes at least one inward directed engagement member for engaging said female connector in said initial non ready for reconstitution state for assembling said male vial adapter on said female vial adapter.

7. The assembly according to claim 5, wherein said male vial adapter includes at least two axial directed grip members lateral to said male connector and having inward directed projections for engaging said female connector's free end on said axial displacement of said male vial adapter towards said female vial adapter.

8. The assembly according to claim 1, wherein said female connector includes an internal annular seal for sealing engagement with said male connector during reconstitution of liquid drug contents and an IV spike during liquid drug administration.

9. The assembly according to claim 1, wherein said female connector includes a manually placed cap for sealing said female connector subsequent to said complete mechanical detachment of said male vial adapter from said female vial adapter.

10. The assembly according to claim 1, wherein said venting arrangement includes at least one hooded vent port having a vent aperture facing radial outward with respect to said longitudinal axis.

* * * * *